United States Patent [19]

Cain et al.

[11] Patent Number: 5,296,479
[45] Date of Patent: Mar. 22, 1994

[54] TREATMENT OF PSYCHOSIS USING 1-CYCLOALKYLPIPERIDINES

[75] Inventors: Gary A. Cain, New Castle; Paul J. Gilligan, Claymont; Sang W. Tam, Hockessin, all of Del.

[73] Assignee: The Du Pont Merck Pharmaceutical Company, Wilmington, Del.

[21] Appl. No.: 831,887

[22] Filed: Feb. 6, 1992

Related U.S. Application Data

[60] Division of Ser. No. 570,199, Aug. 20, 1990, Pat. No. 5,109,002, which is a continuation-in-part of Ser. No. 404,813, Sep. 8, 1989, abandoned.

[51] Int. Cl.$^5$ ............................................. A61K 31/445
[52] U.S. Cl. ...................... 514/256; 514/306; 514/314; 514/317; 514/318; 514/323; 514/326; 514/415; 514/419
[58] Field of Search ............... 514/256, 306, 314, 317, 514/318, 323, 326, 415, 419

[56] References Cited

U.S. PATENT DOCUMENTS 4,294,841 10/1981 Champsiex et al. ............... 546/236

OTHER PUBLICATIONS

CA95:24830h, Eistetter et al, 1981.
J. Med. Chem. 15(6), Irwin et al, pp. 690–692, 1972.
CA96:123074s, Trijzelaar et al, 1982.

Primary Examiner—C. Warren Ivy
Assistant Examiner—Ba K. Trinh
Attorney, Agent, or Firm—Blair Q. Ferguson; Margaret A. Horn

[57] ABSTRACT

There are provided cycloalkyl piperidine compounds which are useful in the treatment of physiological or drug-induced psychosis or dyskinesia in a mammal. These novel compounds are selective sigma receptor antagonists and have a low potential for movement disorder side effects associated with typical antipsychotic agents.

25 Claims, No Drawings

TREATMENT OF PSYCHOSIS USING 1-CYCLOALKYLPIPERIDINES

RELATED APPLICATION

This is a division of application Ser. No. 07/570,199, filed Aug. 20, 1990, now U.S. Pat. No. 5,109,002, which is a continuation-in-part of application Ser. No. 07/404,813, filed Sep. 8, 1989 now abandoned.

FIELD OF THE INVENTION

This invention relates to novel cycloalkylpiperidine compounds, pharmaceutical compositions containing them and methods of using these compounds to treat physiological or drug induced psychosis and as antidyskinetic agents.

BACKGROUND OF THE INVENTION

U.S. Pat. No. 4,225,608 (Uhl et al.) discloses phenoxyalkylamines of the formula:

AR—O—R wherein:
Ar is phenyl optionally substituted with 1 or 2 substituents selected from the group:
F, Cl, Br, alkyl or alkoxy each of 1 to 4 carbon atoms, cycloalkoxy of 3 to 6 carbon atoms, $CF_3$, CN, alkylthio of 1 to 4 carbon atoms, $SCF_3$, OH or alkanoyloxy of 1 to 10 carbon atoms;
R is (1-$R^1$-2-pyrrolidyl)—$CH_2$—$CHR^2$—, (1-$R^1$-2-piperidyl)-$CH_2$—$CHR^2$— or 1-$R^1$-3-Z-4-hexahydroazepinyl;
$R^1$ is H, alkyl or alkenyl each of up to 4 carbon atoms, cyclopropylmethyl or benzyl;
$R^2$ is H, alkyl of 1 to 4 carbon atoms or phenyl; and
Z is alkyl of 1 to 4 carbon atoms with the proviso that Ar is p-fluorophenyl only if R is not 2-(1-methyl-2-piperidyl)-ethyl. The phenoxyalkylamine compounds have antidepressant activity.

Japanese patent 48-40779 (Dainippon) describes the process for preparing compounds of the formula:

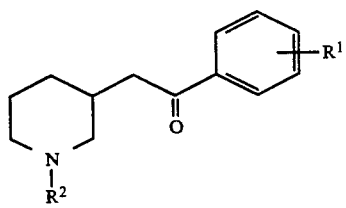

wherein:
$R^1$ is H, halogen, alkyl, alkoxy or trihalomethyl; and
$R^2$ is alkyl, alkenyl, hydroxyalkyl, cycloalkylalkyl, dimethylaminoalkyl, aralkyl, arylalkenyl, arylalkoxy, aryloxyalkyl, 2-halophenothiazinyl(10)-propyl, 10, 11-dihydro-5H-dibenzo (b,f)azepin-5-ylpropyl or 3-halo-10,11-dihydro-5H-dibenzo (b,f)azepinyl propyl.

These compounds are described as being useful as pharmaceuticals since they exhibit psychotropic effects, however, no utility is actually documented.

Nagai et al. (Dainippon) describe psychotropic compounds of the formula:

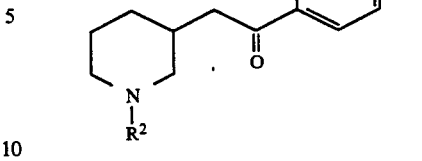

wherein:
$R^1$ is H, Cl or F; and
$R^2$ is alkyl, alkenyl, benzyl, phenethyl, hydroxyethyl, cyclopropylmethyl or substituted phenylalkyl.
See: Chemical Pharmaceutical Bulletin 25(8) 1911-1922 (1979).

The 3-isomers described in Japanese Patent 48-40779 and in the Chemical Pharmaceutical Bulletin, cited above, do not show the sigma receptor selectivity demonstrated by the compounds of the present invention. It is this sigma receptor selectivity of the compounds of the present invention which makes them so advantageous over the compounds in the prior art. Traditionally, antipsychotic agents have been potent dopamine receptor antagonists. For example, phenothiazines such as chlorpromazine and most butyrophenones such as haloperidol are potent dopamine receptor antagonists. These dopamine receptor antagonists are associated with a high incidence of side effects, particularly Parkinson-like motor effects or extra-pyramidal side-effects (EPS), and dyskinesias including tardive dyskinesias at high doses. Many of these side effects are not reversible even after the dopamine receptor antagonist agent is discontinued.

The present invention is related to antipsychotic agents which are selective sigma receptor antagonists rather than the traditional dopamine receptor blockers known in the art, and therefore the compounds of the present invention have low potential for the typical movement disorder side-effects associated with the dopamine antagonist antipsychotic agents while they maintain the ability to antagonize aggressive behavior and antagonize hallucinogenic-induced behavior.

SUMMARY OF THE INVENTION

The antipsychotic compounds of the the present invention are cycloalkylpiperidines of the formula:

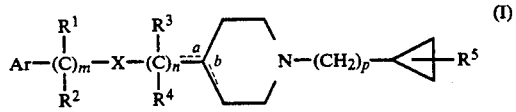

or a pharmaceutically acceptable salt thereof, wherein:
m is 0 to 3;
n is 0 to 3;
provided that m and n are not both O;
p is 0 to 3;
X is O, S, SO, $SO_2$, $NR^6$, $CR^7R^8$,

or CHOH;
$R^1$, $R^3$ and $R^7$ independently are H, alkyl of 1 to 5 carbon atoms, halogen, $NR^{10}R^{11}$, OH, $CO_2H$, carboalkoxy of 2 to 6 carbon atoms, CN, $Ar^1$, alkoxy of 1 to 5 carbon atoms or alkylthio of 1 to 5 carbon atoms;

$R^2$, $R^4$ and $R^8$ independently are H, alkyl of 1 to 5 carbon atoms, carboalkoxy of 2 to 6 carbon atoms, CN, alkoxy of 1 to 5 carbon atoms or $Ar^1$;

provided that $R^1$, $R^2$, $R^3$ and $R^4$ are not alkoxy of 1 to 5 carbon atoms, alkylthio of 1 to 5 carbon atoms, $NR^1OR^{11}$ or OH when X is O, S, SO, $SO_2$ or $NR^6$;

$R^5$ is H, alkyl, halogen, OH or alkenyl;

$R^6$ is H, alkyl of 1 to 5 carbon atoms or $Ar^1$;

Ar and $Ar^1$ independently are naphthyl, pyridyl, pyrimidyl, indolyl, quinolinyl, isoquinolinyl, or phenyl optionally substituted with alkyl of 1 to 3 carbon atoms, alkoxy of 1 to 3 carbon atoms, haloalkyl of 1 to 3 carbon atoms and 1 to 7 halogen atoms, SH, $S(O)_t$ alkyl of 1 to 3 carbon atoms, where t is 1, 2 or 3, dialkylamino of 2 to 6 carbon atoms, halogen, OH, alkylamino of 1 to 3 carbon atoms, $NH_2$, CN, $NO_2$, $SO_3H$, tetrazole, $CO_2H$, carboalkoxy of 2 to 6 carbon atoms, $CONH_2$, $SO_2NH_2$, $COR^9$, $CONR^{12}R^{13}$, $SO_2NR^{12}R^{13}$, $Ar^2$, $OAr^2$ or $SAr^2$;

$Ar^2$ is naphthyl or phenyl optionally substituted with alkyl of 1 to 3 carbon atoms, haloalkyl of 1 to 3 carbon atoms and 1 to 7 halogen atoms, alkoxy of 1 to 3 carbon atoms, halogen or alkylthio of 1 to 3 carbon atoms;

$R^9$, $R^{10}$, $R^{11}$, $R^{12}$ and $R^{13}$ independently are H, alkyl of 1 to 5 carbon atoms or phenyl or $R^{10}$ and $R^{11}$ taken together are an alkylene chain of 3 to 6 carbon atoms or $R^{12}$ and $R^{13}$ taken together are an alkylene chain of 3 to 6 carbon atoms; and a or b is a double bond or a single bond, provided that both are not double bonds.

Preferred compounds in the present invention are those compounds of Formula (I) wherein:

X is

CHOH or O; and/or m is 0; and/or n and p are 1; and/or $R^3$–$R^5$ are H; and/or Ar is phenyl optionally substituted with halogen, $OCH_3$, $NH_2$, $NO_2$ or another phenyl group.

Specifically preferred compounds of the present invention are:

a) 1-(cyclopropylmethyl)-4-(2'-(4''-fluorophenyl)-2'-oxoethyl) piperidine b) 1-(cyclopropylmethyl)-4-(2'-(4''-fluorophenyl)-2'-oxoethyl) piperidine, hydrobromide salt c) 1-(cyclopropylmethyl)-4-(2'-(4''-chlorophenyl)-2'-oxoethyl) piperidine d) 1-(cyclopropylmethyl)-4-(2'-(4''-chlorophenyl)-2'-oxoethyl) piperidine, hydrobromide salt e) 1-(cyclopropylmethyl)-4-(4'-fluorophenoxymethyl)-piperidine f) 1-(cyclopropylmethyl)-4-(4'-fluorophenoxymethyl)-piperidine, hydrochloride salt g) 1-(cyclopropylmethyl)-4-(4'-chlorophenoxymethyl)-piperidine h) 1-(cyclopropylmethyl)-4-(4'-chlorophenoxymethyl)-piperidine, hydrochloride salt i) 1-(cyclopropylmethyl)-4-(4'-nitrophenoxymethyl)-piperidine j) 1-(cyclopropylmethyl)-4-(2'-(4''-biphenyl)-2'-oxoethyl)piperidine k) 1-(cyclopropylmethyl)-4-(2'-(4''-biphenyl)-2'-oxoethyl)piperidine, hydrobromide salt.

Also provided in the present invention are pharmaceutical compositions comprising an effective amount of a compound of Formula (I) and a pharmaceutically acceptable carrier.

Further provided are methods of using the compounds of Formula (I) for the treatment of physiological or drug-induced psychosis in a mammal as well as for the treatment of dyskinesias in a mammal.

Furthermore, there are provided, processes for the preparation of compounds of Formula (I).

In addition, there are provided novel intermediate compounds and methods of preparing them, useful for the preparation of some of the active compounds of this invention; said intermediate compounds having the formula:

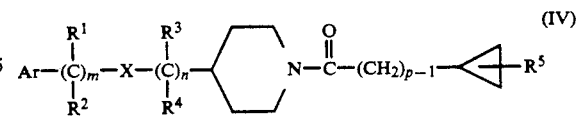

wherein:

m is 0 to 3;

n is 0 to 3;

provided that m and n are not both 0;

p is 1 to 3;

X is O, S, $NR^6$;

Ar and $Ar^1$ independently are naphthyl pyridyl, pyrimidyl, quinolinyl, isoquinolinyl or phenyl optionally substituted with alkyl of 1 to 3 carbon atoms, alkoxy of 1 to 3 carbon atoms, haloalkyl of 1 to 3 carbon atoms and 1 to 7 halogen atoms, $S(O)_t$ alkyl of 1 to 3 carbon atoms, where t is 1, 2 or 3, dialkylamino of 2 to 6 carbon atoms, halogen, alkylamino of 1 to 3 carbon atoms, CN, $NO_2$, carboalkoxy of 2 to 6 carbon atoms, $COR^9$, $CONR^{12}R^{13}$, $SO_2NR^{12}R_{13}$, $Ar^2$, $OAr^2$ or $SAr^2$;

$Ar^2$ is naphthyl or phenyl optionally substituted with alkyl of 1 to 3 carbon atoms, haloalkyl of 1 to 3 carbon atoms and 1 to 7 halogen atoms, alkoxy of 1 to 3 carbon atoms, halogen or alkylthio of 1 to 3 carbon atoms;

$R^1$–$R^4$ and $R^6$ independently are H, alkyl of 1 to 5 carbon atoms or $Ar^1$;

$R^5$ is H, alkyl, halogen, OH or alkenyl; and $R^9$, $R^{12}$ and $R^{13}$ independently are H, alkyl of 1 to 5 carbon atoms or phenyl, or $R^{12}$ and $R^{13}$ taken together are an alkylene chain of 3 to 6 carbon atoms.

DETAILED DESCRIPTION OF THE INVENTION

Compounds of Formula (I) may be prepared according to Scheme I. In Scheme I, a compound of Formula (II) [where X is O, S, $NR^6$ or $CH_2$ (when m=1 and $CR^1R^2$=CO) or a single bond (when m=1)] is treated with a base in an inert solvent then reacted with a compound of Formula (III) to afford a compound of Formula (IV). Bases which may be used for this reaction include, but are not limited to, alkali metal hydrides, preferably sodium hydride, alkali metal carbonates, preferably potassium carbonate, alkali metal dialkylamides, preferably lithium di-isopropylamide, alkali metal bis(trialkylsilyl) amides, preferably sodium bis(trimethylsilyl)amide, alkyl alkali metal compounds (such as butyl lithium), alkali metal alkoxides (such as sodium ethoxide), alkyl alkaline earth metal halides (such as methyl magnesium bromide), trialkylamines (such as triethylamine or di-isopropylethylamine), polycyclic di-amines (such as 1,4 diazabicyclo [2.2.2]octane or 1,8-diazabicyclo-[5.4.0]undecene) or quaternary ammonium salts (such as Triton B). The choice of inert solvent must be compatible with the choice of base (see J. March, Advanced Organic Chemistry (New York:J. Wiley and Sons, 1985) pp. 255–446; H. O. House, Modern Synthetic Reactions (New York:W. A. Benjamin Inc., 1972, pp. 546–553)). Solvents include lower alkyl alcohols of 1 to 6 carbons, dialkyl ethers of 4 to 10 carbons, cyclic ethers of 4 to 10 carbons, preferably tetrahydrofuran or dioxane, dialkylformamides, preferably N,N-dimethylformamide, dialkylacetamides, preferably N,N-dimethylacetamide, cyclic amides, preferably N-methylpyrrolidinone, hydrocarbons of 5 to 10 carbons or aromatic hydrocarbons to 6 to 10 carbons. The leaving group Y in Formula (III) may be halide, arylsulfonyloxy, preferably p-toluenesulfonyloxy, alkylsulfonyloxy (such as methanesulfonyloxy), haloalkylsulfonyloxy, preferably trifluoromethylsulfonyloxy or acyloxy, preferably acetoxy. Reaction temperatures range from about $-78°$ to $200°$ C., preferably about $50°-100°$ C. Compounds of Formula (IV) may be treated with reducing agents in inert solvents to afford compounds of Formula (I). Such reducing agents include but are not limited to, alkali metal aluminum hydrides, preferably lithium aluminum hydride, alkali metal borohydrides, preferably lithium borohydride, alkali metal trialkoxyaluminum hydrides (such as lithium tri-t-butoxyaluminum hydride), dialkylaluminum hydrides (such as di-isobutylaluminum hydride), borane, dialkylboranes (such as di-isoamyl borane), alkali metal trialkylboron hydrides (such as lithium triethylboron hydride). Inert solvents include lower alkyl alcohols of 1 to 6 carbons, ethereal solvents (such as diethyl ether or tetrahydrofuran), aromatic or non-aromatic hydrocarbons of 6 to 10 carbons. Reaction temperatures for the reduction range from about $-78°$ to $200°$ C., preferably about $50°$ to $120°$ C. The choice of reducing agent and solvent is known to those skilled in the art as taught in the above cited March reference (pp. 1093-1110).

SCHEME I

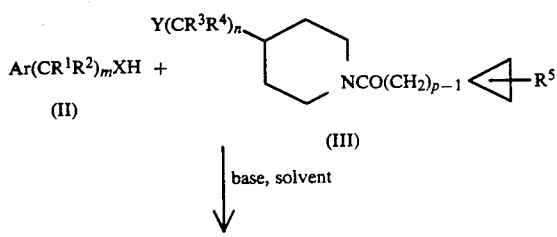

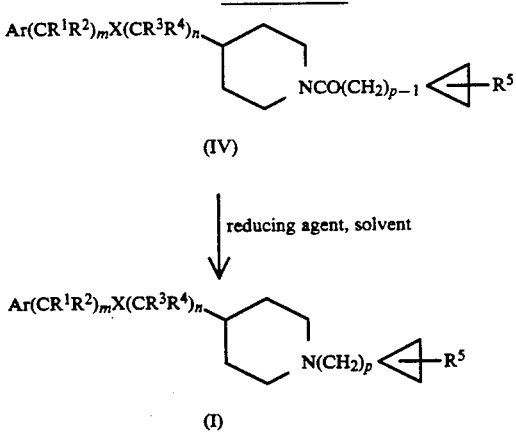

In Scheme II, a compound of Formula (II) (X=O, S, $NR^6$) is reacted with a compound of Formula (V) in the presence of a triarylphosphine, (Ar''3P), preferably triphenylphosphine and an azodicarboxylate diester ($RO_2CN=NCO_2R$) wherein R is lower alkyl, and preferably diethyl azodicarboxylate in an inert solvent, preferably tetrahydrofuran or benzene. Reaction temperatures range from about $50°$ to $80°$ C. The choices of triaryl phosphine, solvent or azodicarboxylate ester are known to those skilled in the art as described by O. Mitsunobu (Synthesis, 1 [1981]).

SCHEME II

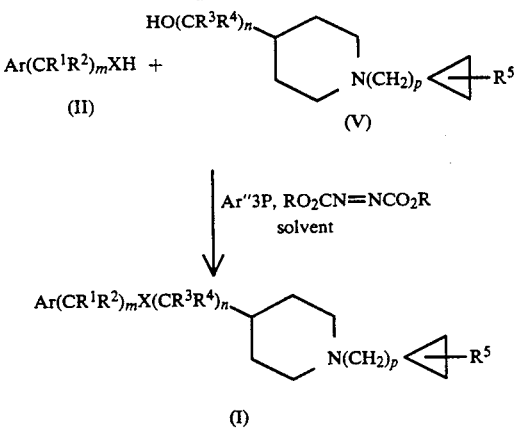

In Scheme III a pyridine derivative of Formula (VII) is converted to its metallo derivative (VII*) by treatment with a metallating agent. For the case where $n=1$ or Y=H, such metallating agents are bases, which include but are not limited to, alkali metal dialkylamides, preferably lithium di-isopropylamide, alkali metal bis(trialkylsilyl)amides, preferably lithium or sodium bis(trimethylsilyl)amides, alkali metal alkoxides, alkali metal hydrides, alkyl alkaline earth metal halides (such as methyl magnesium bromide). For the cases where n is not equal to 1 or Y is halogen, preferably Cl or Br, metallating agents include alkali metals, such as lithium, alkaline earth metals, such as magnesium, or alkyl lithiums, such as n-butyl lithium. Metallating agents include combinations of one of the above reagents and an inorganic salt such as alkaline earth metal halides or transition metal halides, preferably $CuBr$, $ZnCl_2$ or $CeCl_3$. The metallo derivative of (VII), i.e. (VII*) may be formed in an inert solvent such as lower alkyl alcohols of 1 to 6 carbons, ethereal solvents, such as tetrahydrofuran or 1,2-dimethoxyethane, or aromatic or non-aromatic hydrocarbons of 6 to 10 carbon atoms. Temperatures for the metallation range from about −80° C. to 200° C., preferably about −78° to 70° C. once the metallo derivative of (VII), i.e. (VII*) is formed, it is reacted in the same solvent with a compound of Formula (VI) (where R is alkoxyl of 1 to 6 carbons or halogen) to afford a compound of Formula (VIII). Reaction temperatures range from about −78° to 70° C., preferably about 0° to 70° C. A compound of Formula (VIII) is then converted to a compound of Formula (X) upon treatment with an alkylating agent of Formula (IX) (Z=halogen, alkylsulfonyloxy, or haloalkylsulfonyloxy). Such alkylation can be conducted with or without an inert solvent. When an inert solvent is used, such solvent may be a lower alkyl alcohol of 1 to 6 carbons, an alkanenitrile, preferably acetonitrile, a halocarbon of 1 to 6 carbons, a dialkylformamide of 2 to 6 carbons, a dialkylacetamide of 3 to 7 carbons or an aromatic or non-aromatic hydrocarbon of 6 to 10 carbons. The intermediate (X) may be isolated upon removal of volatiles, chromatography or crystallization or (X) may be carried on to the next step in Scheme III if it is hygroscopic. Treatment of a compound of Formula (X) with a reducing agent yields a compound of Formula (I) (where X=CHOH or C=O [depending on the reducing agent]). Reducing agents include molecular hydrogen and a noble metal catalyst, preferably palladium on carbon or platinum IV oxide, alkali metal aluminum hydrides, preferably lithium aluminum hydride, alkali metal trialkoxyaluminum hydrides, dialkylaluminum hydrides, alkali metal borohydrides, preferably sodium borohydride, dialkylboron hydrides, diimide and its precursors, alkali metal cyanoborohydrides, preferably sodium cyanoborohydride, zinc amalgam or zinc metal. It will be apparent to those skilled in the art that some of the above reagents by themselves will only partially reduce the pyridine ring to give tetrahydropyridines among other products (See generally: the above cited March reference, pp. 1093–1110), for example structure (X'):

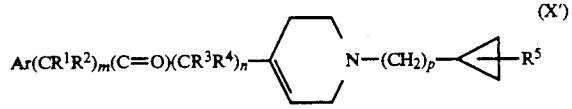

In these cases, combinations of the above reagents either in tandem or sequentially must be used. Inert solvents include, but are not limited to, lower alkyl alcohols, ethereal solvent such as diethyl ether or tetrahydrofuran, aromatic or non-aromatic hydrocarbons of 6 to 10 carbons.

SCHEME III

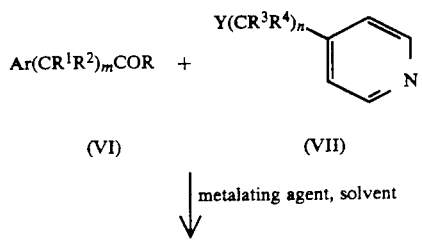

-continued
SCHEME III

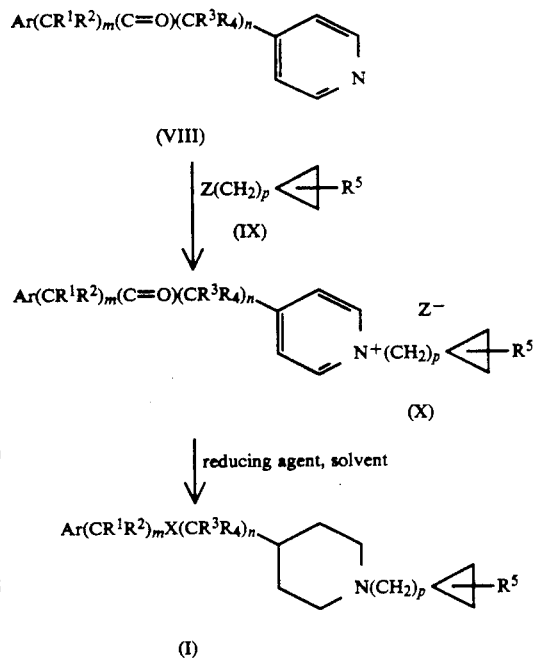

According to Scheme IV, an ester of Formula (XI) (R is alkyl of 1 to 6 carbons or aralkyl of 7 to 10 carbons) is treated with an alkylating agent of Formula (IX) in the presence of a base and an inert solvent. The bases and inert solvents that may be used are the same as those defined for the first reaction step of Scheme I. The resulting ester of Formula (XII) is then converted to an aldehyde of Formula (XIII) either directly using a reducing agent or indirectly using a reducing agent then an oxidizing agent in sequence. In the latter course, the intermediate alcohol (XIV) may or may not be isolated depending on its stability using standard techniques known to those skilled in the art. Reducing agents and the inert solvents for the reduction include those defined in Schemes I and III. Oxidizing agents for converting an alcohol of Formula (XIV) to an aldehyde of Formula (XIII) include transition metal oxides, such as $CrO_3$ or $MnO_2$, pyridine-chromium complexes, such as $CrO_3.C_5H_5N$, pyridinium dichromate or pyridinium chlorochromate, an oxalylchloride-dimethylsulfoxide-triethylamine reagent system, commonly called the Swern oxidation system (D. Swern et al., J. Organic. Chem., 43, 2480–2482 (1978)) or a dimethyl sulfoxide-dicyclohexylcarbodiimide system (See: H. O. House, Modern Synthetic Reactions (New York:W. A. Benjamin Inc., 1972) pp. 416–421). Such oxidations, when necessary, employ an inert solvent such as those employed for the reduction or halocarbons of 1 to 6 carbons, preferably dichloromethane or 1,2-dichloroethane. A compound of Formula (XIII) is then converted to a compound of Formula (XVI) [Formula (I) where X=CHOH] by reaction with a metallo derivative of a compound of Formula (XV). Such a metallo derivative is prepared by treatment with a base (X=H) or other metallating agents (X=halogen). Metallating agents, and the inert solvents for such metallations, include those defined for the first step of Scheme III. A compound of Formula (XVI) [Formula (I) where X=CHOH] is oxidized to a compound of Formula (XVII) (Formula (I) where X=CO] using an oxidizing agent and inert solvent, both of which are defined the same as for the second step of Scheme IV.

SCHEME IV

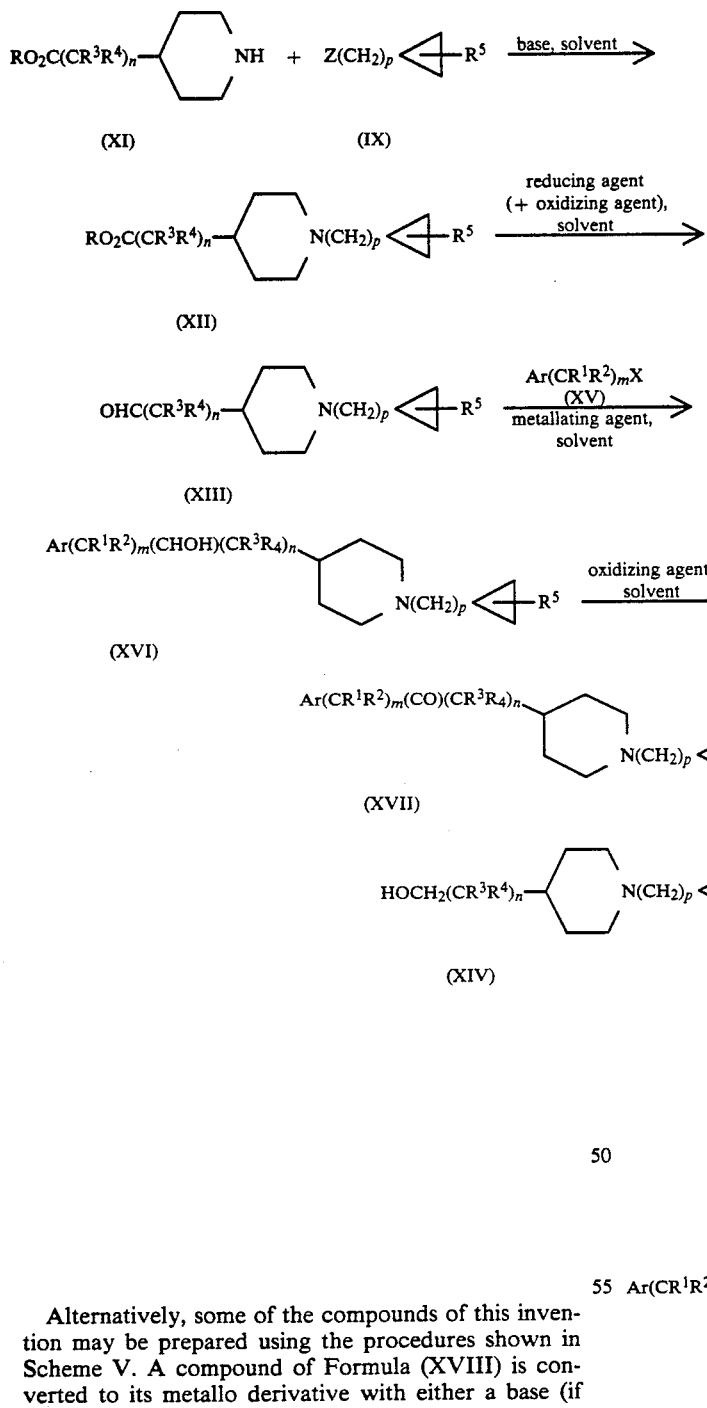

SCHEME V

Alternatively, some of the compounds of this invention may be prepared using the procedures shown in Scheme V. A compound of Formula (XVIII) is converted to its metallo derivative with either a base (if Y=H, halogen) or other metallating agents (if Y=halogen) in an inert solvent. The choices of metallating agent and inert solvent are defined as for the first step of Scheme III. Such a metallo derivative is reacted with an aldehyde of Formula (XIX) in the same inert solvent to afford a compound of Formula (XVI) [Formula (I) where X=CHOH]. Reaction temperatures range from about −100° to 200° C. preferably about −78° to 80° C.

Some of the compounds of this invention may be prepared according to Scheme VI. A compound of Formula (XVII) [Formula (I) where X=CO] is reacted with an amine of Formula $HNR^{10}R^{11}$ in the presence of a reducing agent in an inert solvent to give a compound of Formula (XX) [Formula (I) where $X=CHNR^{10}R^{11}$]. The choices of reducing agent and inert solvent are defined the same as for these in the last step of Scheme III. $R^{10}$ and $R^{11}$ independently may be H or alkyl of 1 to 6 carbons or taken together are an alkylene chain of 2 to 6 carbons. When $R^{10}$ and $R^{11}$ are both H, an ammonium salt is used (preferably ammonium acetate) according to the prior art (see pp. 45-100 of House, Modern Synthetic Reaction, cited supra).

SCHEME VI

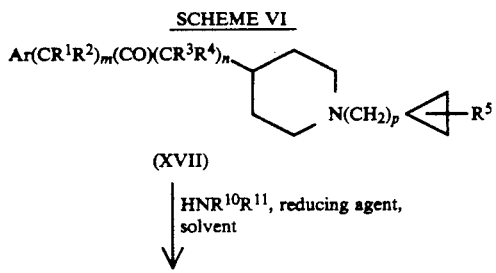

According to Scheme VII, a compound of Formula (XVI) [Formula I where X=CHOH] is treated with a sulfonylating agent, preferably methanesulfonyl chloride, p-toluenesulfonyl chloride or trifluoromethanesulfonic anhydride, in the presence of a base, such as a trialkylamine, preferably triethylamine, an alkali metal hydride, preferably sodium hydride, an aromatic amine, preferably pyridine, or an alkali metal carbonate or alkoxide. Such a sulfonylation is performed in an inert solvent such as a halocarbon of 1 to 6 carbons, preferably dichloromethane, ethereal solvents, such as diethylether or tetrahydrofuran, aromatic or non-aromatic hydrocarbons of 6 to 10 carbons, or alkanenitriles, preferably acetonitrile. A compound of Formula (XXI) [preferably where X is $O_2SCH_3$, $O_2SC_6H_4$-$CH_3$-p or $O_2SCF_3$] is formed from such a sulfonylation and then is reacted with a nucleophilic reagent in an inert solvent to afford a compound of Formula (XXII) [Formula (I) where X is $CHR^7$]. Such nucleophilic reagents include alkali metal alkoxides, alkali metal aluminum hydrides, dialkyl aluminum hydrides, dialkylboranes, alkyl alkaline earth halides, preferably alkyl magnesium halides, dialkyl lithium cuprates, amines of the formula $HNR^{10}R^{11}$, wherein $R^{10}$ and $R^{11}$ are as defined above, alkali metal cyanides or alkali metal alkylsulfides. Inert solvents include lower alkyl alcohols, alkanenitrile, preferably acetonitrile, ethereal solvents, such as diethyl ether and tetrahydrofuran, aromatic or non-aromatic hydrocarbons of 6 to 10 carbon atoms.

According to Scheme VIII, a compound of Formula (XVII) [Formula (I) where X=CO] is reacted with a nucleophilic reagent in an inert solvent to give a compound of Formula (XXIII) [Formula (I) where $X=CR^6R^7$ where $R^6$ and $R^7$ are as defined in Formula (I)]. The choice of solvent is defined the same as for those in Scheme VII. The nucleophilic reagents include alkali metal hydrides, dialkyl aluminum hydrides, trialkyl aluminum compounds, aryl or alkyl alkaline earth halides (preferably aryl or alkyl magnesium halides), aryl or alkyl lithiums or dialkyllithium cuprates.

SCHEME VI

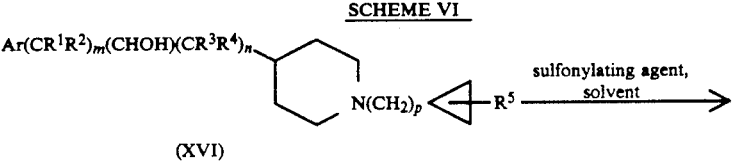

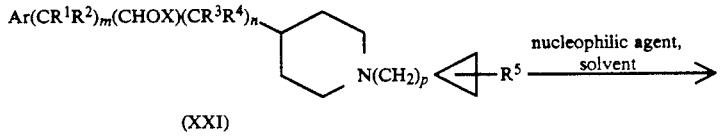

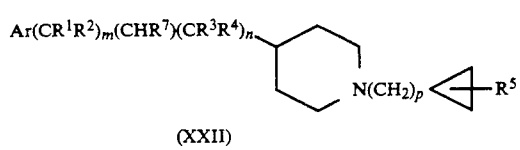

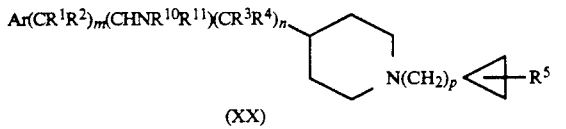

SCHEME VIII

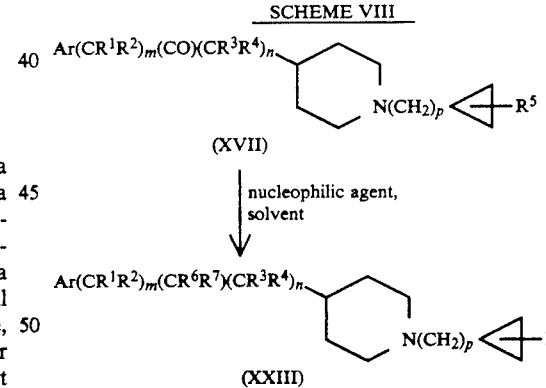

According to Scheme IX an acid derivative of Formula (XXIV) [R is halogen, OH or lower alkoxy and Ar and $R^3$ and $R^4$ are as defined in Formula (i)] is reacted with an aromatic compound in the presence of a Lewis acid in an inert solvent to afford a compound of Formula (XXV). Lewis acids include aluminum halides, alkylsulfonic acids, preferably methanesulfonic acid, polyphosphoric acid, or acetic acid. Inert solvents include carbon disulfide or aromatic hydrocarbons of 6 to 10 carbons bearing electron-withdrawing substituents, such as nitrobenzene. Compounds of Formula (XXV) are then converted to pyridinium salts (XXVI) with alkylating agents (IX). These compounds of Formula (XXVI) are then treated with reducing agents in an inert solvent to afford compounds of Formula (XXVII)

[Formula (I), wherein m is O and X is CO]. The choices of alkylating agent (IX), reducing agent, inert solvents and reaction temperatures are the same as those defined in Scheme III.

SCHEME IX

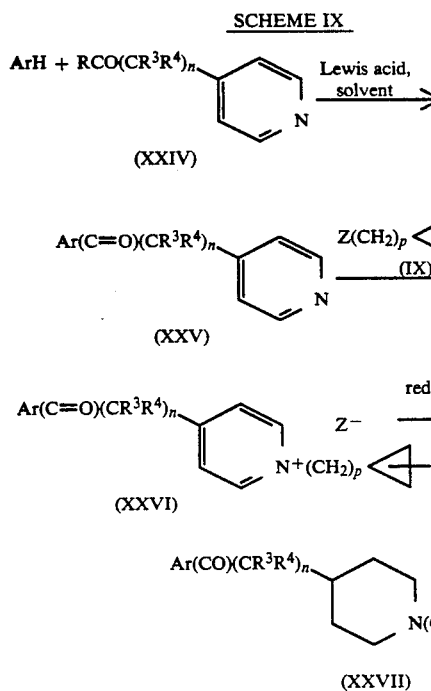

Alternatively, according to Scheme X, a compound of Formula (XXVIII) is reacted with an aromatic compound in the presence of a Lewis acid and an inert solvent to provide a compound of Formula (XXIX). The choices of Lewis acid and inert solvents are defined the same as those in Scheme IX. Reaction temperatures range from about 0° to 150° C. Compounds of Formula (XXIX) may be treated with reducing agents in inert solvents to give compounds of Formula (XXX) [Formula (I) wherein m is O and X is CHOH]. The choices of reducing agent, solvent and reaction temperature are defined the same as those for the second step of Scheme I. Compounds of Formula (XXX) may be oxidized to compounds of Formula (XXXI) [Formula (I) wherein m is O and X=CO]. The choices of oxidizing agents, solvents and reaction temperatures are defined the same as those for the oxidation of compounds of Formula (XIV) to compounds of Formula (XIII) in Scheme (IV).

SCHEME X

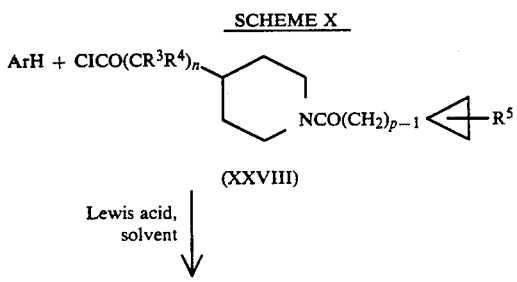

-continued
SCHEME X

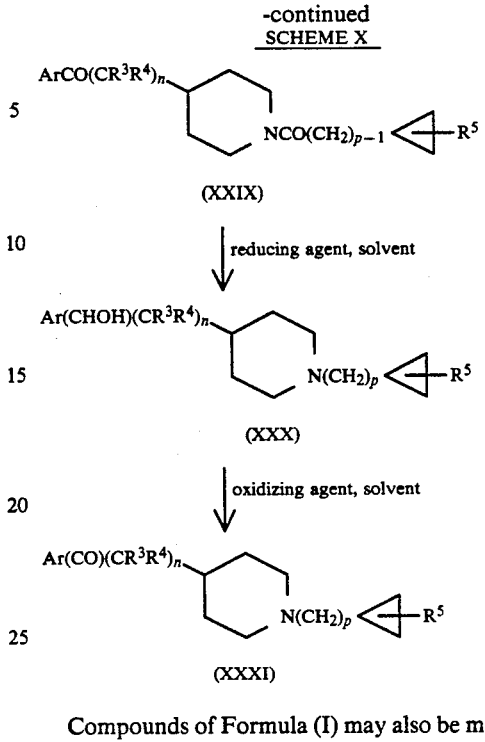

Compounds of Formula (I) may also be made according to Scheme XI. A compound of formula ArZ is reacted with a compound of Formula (XXXII) (X is O, S or NR$^6$) in the presence of a base and an inert solvent to yield a compound of Formula (XXXIII) [Formula (I) wherein m is O]. Ar is preferably a phenyl ring substituted with an electron withdrawing group or a heteroaryl ring. Z is halogen, preferably fluorine or chlorine. The choices for base and solvent are as defined in the first step of Scheme I.

SCHEME XI

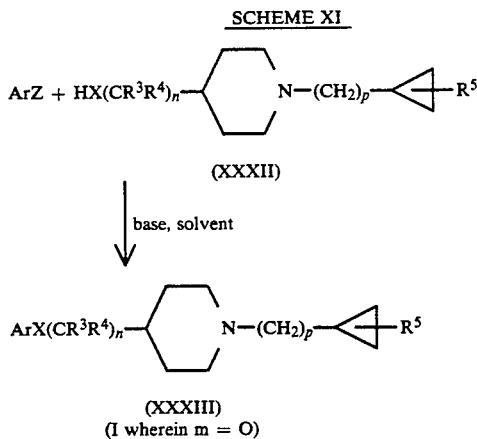

Compounds of Formula (I) may also be prepared according to Scheme XII. A compound of Formula (XXXIV) [wherein Z is halogen, preferably fluorine] is reacted with a compound MY [M is an alkali metal or an alkaline earth metal and Y is a nucleophile selected from the group: azide, alkoxide of 1 to 6 carbon atoms, alkylthioxide of 1 to 6 carbon atoms, cyanide, halide, NH$_2$, alkylamide of 1 to 6 carbon atoms or dialkylamide of 2 to 6 carbon atoms] in an inert solvent at a reaction temperature of about 25°-200° C. and preferably 100°-150° C., to yield a compound of Formula XXXV [Formula I, wherein m is 0 and X is C=O]. The inert solvent may be the same as those defined in the first step of Scheme I. Compounds of formula MY may be generated in situ from a compound of formula HY and a base chosen from the bases defined for the first step of Scheme I.

SCHEME XII

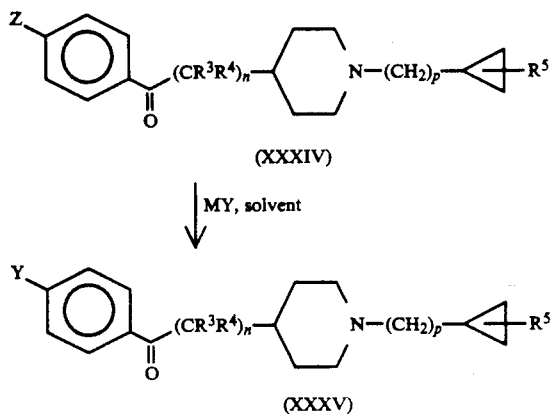

(XXXIV)

↓ MY, solvent (XXXV)

EXPERIMENTAL SECTION

Analytical data were recorded for the compounds described below using the following general procedures. Infrared spectra were recorded on a Perkin-Elmer Model 1600 FT-IR spectrometer; absorbances are recorded in cm$^{-1}$ and intensities are denoted s (strong), m (moderate) and w (weak). Proton NMR spectra were recorded on a IBM-Bruker FT-NMR spectrometer (200 MHz or 300 MHz); chemical shifts were recorded in ppm (δ) from an internal tetramethylsilane standard in deuterochloroform or deuterodimethylsulfoxide and coupling constants (i) are reported in Hz. Mass spectra (MS) or high resolution mass spectra (HRMS) were recorded on Finnegan MAT 8230 spectrometer or Hewlett Packard 5988A model spectrometer. Melting points were recorded on a Buchi Model 510 melting point apparatus and are uncorrected. Boiling points are uncorrected.

Reagents were purchased from commercial sources and, where necessary, purified prior to use according to the general procedures outlined by D. D. Perrin and W. L. F. Armarego, *Purification of Laboratory Chemicals*, 3rd ed., (New York:Pergamon Press, 1988). Chromatography was performed on silica gel using the solvent systems indicated below. For mixed solvent systems, the volume ratios are given. Parts and percentages are by weight unless otherwise specified.

Intermediate compounds of Formula (IV) (where X=O) are exemplified in the following Tables 1-5, these intermediate compounds are then further reduced by various processes to yield some of the active antipsychotic compounds of Formula (I) (Tables 6-10). Compounds of Formula (I) are further exemplified in Tables 11-17.

EXAMPLE 1

Synthesis of
1-(Cyclopropylmethyl)-4-(4-fluorophenoxymethyl)-piperidine

A.

1-(Cyclopropylcarbonyl)-4-hydroxymethylpiperidine

A solution of 1-(cyclopropylcarbonyl)-4-carboethoxy piperidine (35 g, 156 mmol) in anhydrous tetrahydrofuran (350 mi) was stirred at ambient temperature under a nitrogen atmosphere. A solution of lithium borohydride in tetrahydrofuran (2 M, 78 ML, 156 mmol) was added dropwise. Trimethyl borate (1.77 mL, 15.7 mmol) was added, then the reduction mixture was stirred for about 48 hours. Water was added dropwise with vigorous stirring until the vigorous gas evolution ceased. The mixture was diluted twofold with water and extracted three times with ethyl acetate. The combined organic layers were dried over magnesium sulfate, filtered and concentrated in vacuo. Vacuum distillation (bp 165° C., 0.5 mm Hg) gave a clear, colorless liquid (18.2 g):IR (neat): 3410 (br s), 3094 (w), 3008 (s), 2918 (s), 2858 (s), 1738 (m), 1613 (s), 1448 (s), 1375 (s), 1316 (s); $^1$H-NMR: 4.7–4.5 (m, 1H), 4.4–4.1 (m, 1H), 3.6–3.4 (m, 2H), 3.2–2.5 (m, 3H), 2.0–1.7 (m, 4H), 1.4–1.1 (m, 1H), 1.0–0.8 (m, 2H), 0.8–0.65 (m, 2H); HRMS:Calcd for $C_{10}H_{17}NO_2$:183.1259; Found: 183.1250; Anal.:Calcd for $C_{10}H_{17}NO_2$: C, 65.54, H, 9.35, N, 7.64; Found: C, 65.83, H, 9.43, N, 7.50.

B.

1-(Cyclopropylcarbonyl)-4-(methanesulfonyloxy)-piperidine

A solution of 1-(cyclopropylcarbonyl)-4-hydroxymethyl-piperidine from Step A (6.0 g, 33 mmol) and triethylamine (11.9 g, 16.4 mL, 118 mmol) in dichloromethane (150 mi) was stirred at about 0° C. under a nitrogen atmosphere. A solution of methanesulfonyl chloride (4.5 g, 3.0 mL, 39 mmol) in dichloromethane (20 mL) was added dropwise. The reaction mixture was then stirred at about 0°-5° C. for 35 minutes. The pale yellow turbid mixture was poured into a separatory funnel, washed once with a 1N hydrochloric acid solution (ice-cold, 100 mL), twice with a saturated sodium bicarbonate solution (100 mL) and once with brine (100 mL). The organic solution was dried over magnesium sulfate, filtered and concentrated in vacuo to give a pale yellow oil (8.5 g): $^1$H-NMR: 4.8–4.5 (m, 1H), 4.4–4.2 (m, 1H), 4.2–3.95 (m, 2H), 3.2–2.8 (m, 4H), 2.7–2.5 (m, 1H), 2.2–1.6 (m, 4H), 1.5–1.1 (m, 2H), 1.05–0.9 (m, 2H), 0.85–0.7 (m, 2H) ; MS:261.

C.

1-(Cyclopropylcarbonyl)-4-(4'-fluorophenoxymethyl)-piperidine

Sodium hydride (50% in oil, 1.0 g, 20 mmol) was washed with hexanes twice, then suspended in anhydrous tetrahydrofuran (20 mL) with stirring under a nitrogen atmosphere. A solution of 4-fluorophenol (2.13 g, 19 mmol) in tetrahydrofuran (10 mL) was added dropwise with vigorous gas evolution. The reaction mixture was stirred at room temperature for 15 minutes, then a solution of 1-cyclopropylcarbonyl-4-methanesulfonyloxypiperidine (983 mg, 3.77 mmol) from Step B, in tetrahydrofuran (10 mL) was added dropwise. The reaction mixture was then stirred at reflux temperature for about 22 hours, cooled to ambient temperature, poured onto a 2N sodium hydroxide solution and mixed. The aqueous mixture was extracted three times with ether; the combined organic layers were washed with a 2N sodium hydroxide solution, dried over magnesium sulfate and filtered. Solvent was removed in vacuo to give a yellow liquid.

Column chromatography (ethyl acetate) gave, after removal of solvent in vacuo, the product, a clear, colorless liquid (617 mg): $^1$H-NMR: 7.05–6.75 (m, 4H), 4.8-4.55 (br m, 1H), 4.45-4.2 (m, 1H), 3.9-3.6 (br s, 2H), 3.25-3.0 (br t, 1H, J=6), 2.8-2.5 (br t, 1H, J=6), 2.2-1.7 (m, 4H), 1.5-1.2 (m, 2H), 1.05-0.9 (m, 2H), 0.8-0.7 (m, 2H); HRMS:Calcd for $C_{16}H_{20}FNO_2$:277.1478; Found: 277.1466; Anal.:Calcd for $C_{16}H_{20}FNO_2$:C,69.29, H, 7.27, N, 5.05, F, 6.85; Found: C, 69.14, H, 7.41, N, 5.04, F, 7.04.

D.
1-(Cyclopropylmethyl)-4-(4¹-fluorophenoxymethyl)-piperidine

A solution of 1-(cyclopropylcarbonyl)-4-(4¹-fluorophenoxymethyl)piperidine (316 mg, 1.14 mmol) in anhydrous tetrahydrofuran (5 mL) was stirred at ambient temperature under a nitrogen atmosphere. A solution of lithium aluminum hydride in tetrahydrofuran (1 M, 10 mL, 10 mmol) was added dropwise via syringe. The reaction mixture was then stirred at reflux temperature for 24 hours, then it was cooled to room temperature. Ethyl acetate (10 mL) was added dropwise, then water (0.5 mL), a 2N sodium hydroxide solution (0.5 mL), water (1.5 mL) were added sequentially. The resulting suspension was filtered through Celite ® the inorganic salts were washed with copious amounts of ethyl acetate. The filtrate was dried over magnesium sulfate and filtered. Solvent was removed in to give the product, a pale yellow white solid (266 mg, 89% yield): ¹H-NMR:7.0-76.7 (m, 4H), 3.7 (d, 3H, J=7), 3.05 (br d, 2H, J=10), 2.2 (d, 2H, J=7), 2.0-1.6 (m, 4H), 1.5-1.25 (m, 2H), 0.95-0.75 (m, 1H), 0.65-0.5 (m, 2H), 0.1-0.0 (m, 2H); MS:263; Anal.: Calcd. for $C_{16}H_{22}FNO$ $0.5H_2O$: C, 70.50, H, 8.23, N, 5.52; Found: C, 70.49, H, 8.44, N, 5.14.

The compounds of Table 1 may be prepared by the method described in Example 1C using the appropriate hydroxy aromatic compound and the appropriate polar solvent.

TABLE 1

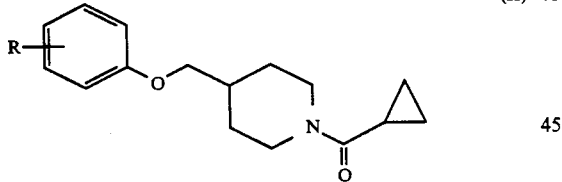
(II)

| Ex. | R | mp (°C.) |
|---|---|---|
| 1C | 4-F | (a) |
| 2 | 4-Cl | 82-83 (b) |
| 3 | 4-CH$_3$O | 54-56 (c) |
| 4 | H | |
| 5 | 4-Br | |
| 6 | 4-I | |
| 7 | 4-NO$_2$ | |
| 8 | 4-(CH$_3$)$_2$N | |
| 9 | 4-NHCOCH$_3$ | |
| 10 | 4-CH$_3$ | |
| 11 | 4-t-C$_4$H$_9$ | 105-109 (d) |
| 12 | 4-C$_2$H$_5$O | |
| 13 | 4-NHCHO | |
| 14 | 4-CO$_2$CH$_3$ | 111-112 (e) |
| 15 | 4-COCH$_3$ | 98-101 (f) |
| 16 | 4-SCH$_3$ | 107-109 (g) |
| 17 | 4-SO$_2$N(CH$_3$)$_2$ | |
| 18 | 4-CF$_3$ | |
| 19 | 4-CCl$_3$ | |
| 20 | 4-CH$_2$CF$_3$ | |
| 21 | 4-COCF$_3$ | |
| 22 | 4-CH$_2$CH$_2$F | |
| 23 | 4-SCOCH$_3$ | |
| 24 | 4-CN | |

TABLE 1-continued

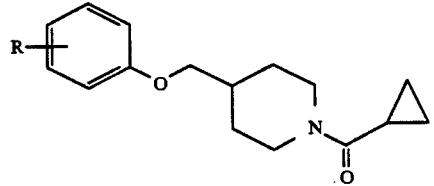
(II)

| Ex. | R | mp (°C.) |
|---|---|---|
| 25 | 4-CON(CH$_3$)$_2$ | |
| 26 | 4-N$_3$ | |
| 27 | 4-CH=CH$_2$ | |
| 28 | 4-C$_6$H$_5$ | (h) |
| 29 | 3-Cl | |
| 30 | 3-Br | |
| 31 | 3-I | |
| 32 | 3-F | |
| 33 | 3-CH$_3$O | |
| 34 | 3-C$_2$H$_5$O | |
| 35 | 3-CH$_3$ | |
| 36 | 3-C$_2$H$_5$ | |
| 37 | 3-CO$_2$CH$_3$ | |
| 38 | 3-COCH$_3$ | |
| 39 | 3-CF$_3$ | |
| 40 | 3-CCl$_3$ | |
| 41 | 3-CH$_2$CF$_3$ | |
| 42 | 3-COCF$_3$ | |
| 43 | 3-CH$_2$CH$_2$F | |
| 44 | 3-CN | |
| 45 | 3-CON(CH$_3$)$_2$ | |
| 46 | 3-CHO | |
| 47 | 3-N$_3$ | |
| 48 | 3-NHCHO | |
| 49 | 3-NHCOCH$_3$ | |
| 50 | 3-NO$_2$ | |
| 51 | 3-(CH$_3$)$_2$N | (i) |
| 52 | 3-SCH$_3$ | |
| 53 | 3-SO$_2$N(CH$_3$)$_2$ | |
| 54 | 3-SCOCH$_3$ | |
| 55 | 2-F | |
| 56 | 2-Br | |
| 57 | 2-Cl | |
| 58 | 2-I | |
| 59 | 2-CH$_3$O | |
| 60 | 2-CH$_3$ | |
| 61 | 2-CO$_2$CH$_3$ | |
| 62 | 2-COCH$_3$ | |
| 63 | 2-CF$_3$ | |
| 64 | 2-CCl$_3$ | |
| 65 | 2-CH$_2$CF$_3$ | |
| 66 | 2-COCF$_3$ | |
| 67 | 2-CH$_2$CH$_2$F | |
| 68 | 2-CN | |
| 69 | 2-CON(CH$_3$)$_2$ | |
| 70 | 2-CHO | |
| 71 | 2-N$_3$ | |
| 72 | 2-NHCHO | |
| 73 | 2-NHCOCH$_3$ | |
| 74 | 2-NO$_2$ | |
| 75 | 2-SCH$_3$ | |
| 76 | 3,4-F$_2$ | (j) |
| 77 | 3,4-Cl$_2$ | (k) |
| 78 | 3,4-(CH$_3$O)$_2$ | |
| 79 | 2,6-Br$_2$-4-CH$_3$ | |
| 80 | 2,6-Br$_2$-4-NO$_2$ | |
| 81 | 2,4-Cl$_2$-6-NO$_2$ | |
| 82 | 2,4-Cl$_2$ | |
| 83 | 3,5-Cl$_2$ | |
| 84 | 3-(C$_2$H$_5$)$_2$N | |
| 85 | 2,4-F$_2$ | |
| 86 | 2,3-F$_2$ | |
| 87 | 2,3-(CH$_3$O)$_2$ | |
| 88 | 3,4-(CH$_3$)$_2$ | |
| 89 | 2,4-(CH$_3$)$_2$ | |
| 90 | 2,4-(NO$_2$)$_2$ | |
| 91 | 3-(OC$_2$H$_5$)-4-OCH$_3$ | |
| 92 | 4-(OCH$_3$)-3-(OC$_2$H$_5$) | |
| 93 | 5-F-2-NO$_2$ | |
| 94 | 2-(CH$_3$O)-4-(NO$_2$) | |

TABLE 1-continued (II)

| Ex. | R | mp (°C.) |
|---|---|---|
| 95 | 3-(CH$_3$O)-4-(NO$_2$) | |
| 96 | 3,4-OCH$_2$O | |
| 97 | 3-CH$_3$-4-NO$_2$ | |
| 98 | 4-CH$_3$-3-NO$_2$ | |
| 99 | 2-CH$_3$-3-NO$_2$ | |
| 100 | 2-NO$_2$-3-CH$_3$ | |
| 101 | F$_5$ | (l) |
| 102 | Br$_5$ | |
| 103 | Cl$_5$ | |
| 104 | 2,3,5,6-F$_4$ | |
| 105 | 2,3,5,6-Cl$_4$ | |
| 106 | 2,3,5,6-Br$_4$ | |
| 107 | 2,4,5-F$_3$ | |
| 108 | 2,4,5-Cl$_3$ | |
| 109 | 2,4,5-Br$_3$ | |
| 110 | 3,4,5-(CH$_3$O)$_3$ | 108–110 (m) |
| 111 | 4-C$_6$H$_5$O | 109–110 (n) |
| 112 | 4-F-C$_6$H$_4$ | 133–135 (o) |
| 113 | 4-CH$_3$O—C$_6$H$_4$ | 143–145 (p) |

Footnotes for Table 1
(a) Anal.: Calcd for C$_{16}$H$_{20}$FNO$_2$: C, 69.29, H, 7.27, N, 5.05, F, 6.85; Found: C, 69.14, H, 7.41, N, 5.04, F, 7.04.
(b) Anal.: Calcd for C$_{16}$H$_{20}$ClNO$_2$: C, 65.41, H, 6.86, N, 4.77, Cl, 12.07; Found: C, 65.18, H, 6.77, N, 4.67, Cl, 12.14.
(c) Anal.: Calcd for C$_{17}$H$_{23}$NO$_3$: C, 70.56, H, 8.01, N, 4.84; Found: C, 70.59, H, 8.02, N, 4.94.
(d) $^1$H-NMR(CDCl$_3$): 7.4–7.2(m, 2H), 6.9–6.7(m, 2H), 4.8–4.6(m, 1H), 3.9–3.7(m, 2H), 3.2–3.0(m, 1H), 2.7–2.5(m, 1H), 2.1–1.7(m, 3H), 1.5–1.3(m, 7H), 1.3(s, 9H); MS: 315.
(e) Anal.: Calcd for C$_{18}$H$_{23}$NO$_4$: C, 68.12, H, 7.30, N, 4.41; Found: C, 68.20, H, 7.48, N, 4.63.
(f) $^1$H-NMR(CDCl$_3$): 8.0(d, 2H, J=8), 6.9(d, 2H, J=8), 4.7(m, 1H), 4.4(m, 1H), 3.9(m, 2H), 3.2(m, 1H), 2.7(m, 1H), 2.6(s, 3H), 2.2–1.7(m, 4H), 1.4(m, 2H); MS: 301.
(g) Anal.: Calcd for C$_{17}$H$_{23}$NO$_2$S: C, 66.85, H, 7.59, N, 4.58, S, 10.67; Found: C, 66.92, H, 7.74, N, 4.46, S, 10.23
(h) $^1$H-NMR(CDCl$_3$): 7.6–7.2(m, 7H), 7.0(d, 2H, J=7), 4.8–4.6(m, 1H), 4.4–4.2(m, 1H), 3.9(br s, 2H), 3.3–3.1(m, 2H), 2.8–2.6(m, 2H), 2.2–1.7(m, 3H), 1.4–1.2(m, 1H), 1.1–0.9(m, 2H), 0.9–0.7(m, 2H).
(i) $^1$H-NMR(CDCl$_3$): 7.15(t, 1H, J=8), 6.15(d, 1H, J=9), 6.1–6.0(m, 2H), 4.7–4.55(m, 1H), 4.35–4.2(m, 1H), 3.9–3.7(m, 2H), 3.2–3.0(m, 1H), 2.9(s, 6H), 2.8–2.5(m, 1H), 2.2–1.7(m, 4H), 1.5–1.2(m, 2H), 1.05–0.9(m, 2H), 0.8–0.65(m, 2H); HRMS: Calcd for C$_{18}$H$_{26}$N$_2$O$_2$: 302.1994; Found: 302.1994.
(j) $^1$H-NMR(CDCl$_3$, 300MHz): 7.05(q, 1H, J=8), 6.75–6.65(m, 1H), 6.65–6.5(m, 1H), 4.75–4.6(m, 1H), 4.4–4.2(m, 1H), 3.85–3.7(m, 2H), 3.15(br t, 1H, J=7), 2.65(br t, 1H, J=7), 2.15–1.7(m, 4H), 1.5–1.2(m, 2H), 1.1–0.9(m, 2H), 0.9–0.75(m, 2H); HRMS: Calcd for C$_{16}$H$_{19}$F$_2$NO$_2$: 295.1384; Found: 295.1385
(k) $^1$H-NMR(CDCl$_3$): 7.4–7.2(m, 1H), 7.05–6.95(m, 1H), 6.8–6.65(m, 1H), 4.8–4.55(m, 1H), 4.4–4.2(m, 1H), 3.9–3.7(m, 2H), 3.3–3.0(m, 1H), 2.8–2.5(m, 1H), 2.2–1.7(m, 4H), 1.5–1.2(m, 2H), 1.06–0.9(m, 2H), 0.85–0.7(m, 2H); HRMS: Calcd for C$_{16}$H$_{19}$Cl$_2$NO$_2$: 327.0793; Found: 327.0788.
(l) $^1$H-NMR(CDCl$_3$): 4.75–4.55(m, 1H), 4.4–4.2(m, 1H), 4.1–3.9(m, 2H), 3.25–3.05(m, 1H), 2.75–2.5(m, 1H), 2.2–1.7(m, 3H), 1.5–1.2(m, 2H), 1.05–0.9(m, 2H), 0.85–0.6(m, 2H); Calcd for C$_{16}$H$_{16}$F$_5$NO$_2$: 329.1101; Found: 349.1100.
(m) Anal.: Calcd for C$_{19}$H$_{27}$NO$_5$: C, 65.31, H, 7.79, N, 4.01; Found: C, 65.41, H, 7.76, N, 4.26.
(n) Anal.: Calcd for C$_{22}$H$_{25}$NO$_2$: C, 75.19, H, 7.17, N, 3.99; Found: C, 75.15, H, 7.12, N, 3.91.
(o) $^1$H-NMR(DMSO, 300MHz): 7.65(dd, 2H, J=8, 6), 7.55(d, 2H, J=8), 7.3(t, 2H, J=8), 7.05(d, 2H, J=8), 4.5–4.3(m, 2H), 3.9(d, 2H, J=7), 3.2–3.0(m, 1H), 2.7–2.55(m, 1H), 2.1–1.7(m, 4H), 1.4–1.05(m, 2H), 0.85–0.6(m, 4H); MS: 354.
(p) $^1$H-NMR(DMSO, 300MHz): 7.55(2 x d, 4H, J=8), 7.0(d, 4H, J=8), 4.5–4.3(m, 2H), 3.9(d, 2H, J=7), 3.8(s, 3H), 3.2–3.1(m, 1H), 2.7–2.6(m, 1H), 2.1–1.75(m, 4H), 1.35–1.1(m, 2H), 0.8–0.6(m, 4H); HRMS: Calcd for C$_{23}$H$_{27}$NO$_3$: 365.1991; Found: 365.2001.

The compounds of Table 2 may be prepared by the method described in Example 1C using the appropriate hydroxy aromatic compound and the appropriate polar solvent.

TABLE 2

(II)

| Ex. | Ar | mp (°C.) |
|---|---|---|
| 114 | 2-naphthyl | 150–152 (a) |
| 115 | 1-naphthyl | |
| 116 | 2,4-dichloro-1-naphthyl | |
| 117 | 4-indolyl | |
| 118 | 5-indolyl | |
| 119 | 5-isoquinolinyl | |
| 120 | 4-pyridyl | (b) |
| 121 | 3-pyridyl | |
| 122 | 2-methyl-4-quinolinyl | |
| 123 | 3-nitro-2-pyridyl | |
| 124 | 4-quinolinyl | (c) |
| 125 | 5-quinolinyl | |
| 126 | 5-pyrimidyl | |

Footnotes for Table 2
(a) Anal.: Calcd for C$_{20}$H$_{23}$NO$_2$.0.2H$_2$O: C, 76.75, H, 7.53, N, 4.47; Found: C, 76.91, 76.89, H, 7.60, 7.53, N, 4.56, 4.32.
(b) $^1$H-NMR(CDCl$_3$): 8.45(d, 2H, J=6), 6.8(d, 2H, J=6), 4.7(br d, 1H, J=10), 4.3(br d, 1H, J=10), 3.95–3.8(m, 2H), 3.15(br t, 1H, J=10), 2.65(br t, 1H, J=10), 2.2–1.75(m, 4H), 1.5–1.25(m, 2H), 1.05–0.95(m, 2H), 0.8–0.65(m, 2H); HRMS: Calcd for C$_{15}$H$_{20}$N$_2$O$_2$: 260.1525; Found: 260.1537.
(c) $^1$H-NMR(CDCl$_3$): 8.7(d, 1H, J=6), 8.2(d, 1H, J=8), 8.05(d, 1H, J=8), 7.7(td, 1H, J=6, 1), 7.5(t, 1H, J=6), 6.7(d, 1H, J=6), 4.75(br d, 1H, J=10), 4.35(br d, 1H, J=10), 4.15–4.0(m, 2H), 3.2(br t, 1H, J=10, 2.7(br t, 1H, J=10); HRMS: Calcd for C$_{19}$H$_{22}$N$_2$O$_2$: 310.1681; Found: 310.1690.

The compounds of Table 3 may be prepared according to the procedure described for Example 1C using the appropriate hydroxymethyl aromatic compound and polar solvent.

TABLE 3

(II)

| Ex. | R | mp (°C.) |
|---|---|---|
| 127 | 4-F | |
| 128 | 4-Cl | |
| 129 | 4-Br | |
| 130 | 4-I | |
| 131 | H | |
| 132 | 4-CH$_3$O | |
| 133 | 4-C$_2$H$_5$O | |
| 134 | 4-TBDMSO | (a) |
| 135 | 4-NO$_2$ | |
| 136 | 4-(CH$_3$)$_2$N | |
| 137 | 4-NHCOCH$_3$ | |
| 138 | 4-N$_3$ | |
| 139 | 4-CH$_3$ | |
| 140 | 4-C$_2$H$_5$ | |
| 141 | 4-CO$_2$CH$_3$ | |
| 142 | 4-COCH$_3$ | |
| 143 | 4-CF$_3$ | |
| 144 | 4-CHO | |
| 145 | 4-CN | |
| 146 | 4-CON(CH$_3$)$_2$ | |
| 147 | 4-SCH$_3$ | |
| 148 | 3-F | |
| 149 | 3-Cl | |
| 150 | 3-Br | |
| 151 | 3-I | |
| 152 | 3-CH$_3$O | |
| 153 | 3-C$_2$H$_5$O | |
| 154 | 3-CH$_3$ | |
| 155 | 3-C$_2$H$_5$ | |
| 156 | 3-CO$_2$CH$_3$ | |
| 157 | 3-COCH$_3$ | |
| 158 | 3-CF$_3$ | |

TABLE 3-continued (II)

| Ex. | R | mp (°C.) |
|---|---|---|
| 159 | 3-CN | |
| 160 | 3-CON(CH$_3$)$_2$ | |
| 161 | 3-CHO | |
| 162 | 3-N$_3$ | |
| 163 | 3-NO$_2$ | |
| 164 | 3-NHCOCH$_3$ | |
| 165 | 3-NHCHO | |
| 166 | 3-(CH$_3$)$_2$N | |
| 167 | 3-SCH$_3$ | |
| 168 | 3-SO$_2$N(CH$_3$)$_2$ | |
| 169 | 2-F | |
| 170 | 2-Cl | |
| 171 | 2-Br | |
| 172 | 2-I | |
| 173 | 2-CH$_3$O | |
| 174 | 2-CH$_3$ | |
| 175 | 2-CO$_2$CH$_3$ | |
| 176 | 2-COCH$_3$ | |
| 177 | 2-CF$_3$ | |
| 178 | 2-CN | |
| 179 | 2-N$_3$ | |
| 180 | 2-NHCHO | |
| 181 | 2-NHCOCH$_3$ | |
| 182 | 2-NO$_2$ | |
| 183 | 2-SCH$_3$ | |
| 184 | 3,4-F$_2$ | |
| 185 | 3,4-Cl$_2$ | |
| 186 | 3,4-(CH$_3$O)$_2$ | |
| 187 | 2,4-Cl$_2$ | |
| 188 | 2,4-F$_2$ | |
| 189 | 2,4-(CH$_3$O)$_2$ | |
| 190 | 3,4-F$_2$ | |
| 191 | 3,5-Cl$_2$ | |
| 192 | 3,4-(CH$_3$)$_2$ | |
| 193 | 2,4-(NO$_2$)$_2$ | |
| 194 | 3,4-(NO$_2$)$_2$ | |
| 195 | 3-CH$_3$O-4-NO$_2$ | |
| 196 | 4-CH$_3$O-3-NO$_2$ | |
| 197 | 3,4-OCH$_2$O— | |
| 198 | F$_5$ | |
| 199 | Cl$_5$ | |
| 200 | 3,4,5-(CH$_3$O)$_3$ | |

Footnote for Table 3
(a) TBDMS = t-butyldimethylsilyl.

The compounds of Table 4 may be prepared according to the method described in Example 1C using the appropriate hydroxy aromatic compound and the appropriate polar solvent.

TABLE 4

(II)

| Ex. | Ar | mp (°C.) |
|---|---|---|
| 201 | 2-naphthyl | |
| 202 | 1-naphthyl | |
| 203 | 2-quinolinyl | |
| 204 | 4-quinolinyl | |
| 205 | 2-pyridyl | |
| 206 | 3-pyridyl | |
| 207 | 4-pyridyl | |
| 208 | 2-pyrimidyl | |
| 209 | 2-furyl | |
| 210 | 2-thienyl | |

The compounds of Table 5 may be prepared according to the method of Example 1C using the appropriate 4-methanesulfonyloxypiperidine derivative.

TABLE 5

(II)

| Ex. | TR | Notes |
|---|---|---|
| 211 | 1-CH$_3$ | |
| 212 | 2-CH$_3$ | (a) |
| 213 | 2,2-Cl$_2$-1-CH$_3$ | (b) |
| 214 | 2,2-(CH$_3$)$_2$-3-(CH=C(CH$_3$)$_2$) | |
| 215 | 2,2(CH$_3$)$_2$-3-(CH=CCl$_2$) | |
| 216 | 2,2-Cl$_2$ | |
| 217 | 2-F | |
| 218 | 2-Cl | |
| 219 | 1-OH | |
| 220 | 2,2,3,3-(CH$_3$)$_4$ | |

Footnotes for Table 5
(a) $^1$H-NMR(CDCl$_3$, 300MHz): 6.95(t, 2H, J=7), 6.8(dd, 2H, J=7, 6), 4.65(br d, 1H, J=8), 4.25(br d, 1H, J=8), 3.9–3.7(m, 2H), 3.15(br t, 1H, J=8), 2.65(br t, 1H, J=8), 2.15–1.8(m, 3H), 1.5–1.1(m, 5H), 1.15(d, 3H, J=7), 0.65–0.45(m, 1H); HRMS: Calcd for C$_{17}$H$_{22}$FNO$_2$: 291.1634; Found: 291.1636.
(b) $^1$H-NMR(CDCl$_3$, 300MHz): 7.05–6.9(m, 2H), 6.9–6.8(m, 2H), 4.65(br t, 1H, J=10), 3.95(br t, 1H, J=10), 3.9–3.75(m, 2H), 3.35–3.2(m, 1H), 2.8–2.65(m, 1H), 2.2–2.0(m, 2H), 2.0–1.9(m, 1H), 1.7–1.2(m, 4H), 1.55(d, 3H, J=7); HRMS: Calcd for C$_{17}$H$_{20}$Cl$_2$FNO$_2$: 359.0855; Found: 359.0860.

Compounds of Formula (I) are exemplified in the following Tables 6–17.

The compounds of Tables 6, 7, 8, 9 and 10 may be prepared employing the procedure described for Example 1D with the appropriate 1-(cyclopropylcarbonyl)-piperidine derivative (Examples 2–220) and the appropriate reducing agent.

TABLE 6

| Ex. | R | mp (°C.) |
|---|---|---|
| 1D | 4-F | (a) |
| 221 | 4-Cl | (b) |
| 222 | 4-CH$_3$O | 37–39 (c) |
| 223 | H | 54–56 (d) |
| 224 | 4-Br | |
| 225 | 4-I | |
| 226 | 4-NH$_2$ | |
| 227 | 4-(CH$_3$)$_2$N | |
| 228 | 4-NHC$_2$H$_5$ | |
| 229 | 4-CH$_3$ | |
| 230 | 4-C$_6$H$_5$ | 81–83 (e) |
| 231 | 4-C$_2$H$_5$O | |
| 232 | 4-NHCH$_3$ | |
| 233 | 4-CH$_2$OH | 120–121 (f) |
| 234 | 4-t-C$_4$H$_9$ | 84–86 (g) |
| 235 | 4-SCH$_3$ | (h) |
| 236 | 4-SO$_2$N(CH$_3$)$_2$ | |
| 237 | 4-CF$_3$ | |
| 238 | 4-CCl$_3$ | |
| 239 | 4-CH$_2$CF$_3$ | |
| 240 | 4-CH(OH)CH$_3$ | 125–127 (i) |
| 241 | 4-CH$_2$CH$_3$F | |
| 242 | 4-SH | |
| 243 | 4-CH$_2$NH$_2$ | (j) |
| 244 | 4-CH$_2$N(CH$_3$)$_2$ | |

TABLE 6-continued

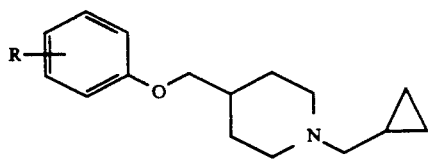

| Ex. | R | mp (°C.) |
|---|---|---|
| 245 | 4-CH=CH₂ | |
| 246 | 3-Cl | |
| 247 | 3-Br | |
| 248 | 3-I | |
| 249 | 3-F | |
| 250 | 3-CH₃O | |
| 251 | 3-C₂H₅O | |
| 252 | 3-CH₃ | |
| 253 | 3-C₂H₅ | |
| 254 | 3-CH₂OH | |
| 255 | 3-CH(OH)CH₃ | |
| 256 | 3-CF₃ | |
| 257 | 3-CH₂CF₃ | |
| 258 | 3-CH(OH)CF₃ | |
| 259 | 3-CH₂CH₂F | |
| 260 | 3-CH₂NH₂ | |
| 261 | 3-CH₂N(CH₃)₂ | |
| 262 | 3-NHCH₃ | |
| 263 | 3-NHC₂H₅ | |
| 264 | 3-NH₂ | |
| 265 | 3-N(CH₃)₂ | |
| 266 | 3-SCH₃ | |
| 267 | 2-F | |
| 268 | 2-Br | |
| 269 | 2-Cl | |
| 270 | 2-I | |
| 271 | 2-CH₃O | |
| 272 | 2-CH₃ | |
| 273 | 2-CH₂OH | |
| 274 | 2-CH(OH)CH₃ | |
| 275 | 2-CF₃ | |
| 276 | 2-CH₂CF₃ | |
| 277 | 2-CH₂NH₂ | |
| 278 | 2-CH₂N(CH₃)₂ | |
| 279 | 2-NHCH₃ | |
| 280 | 2-NHC₂H₅ | |
| 281 | 2-NH₂ | |
| 282 | 2-SCH₃ | |
| 283 | 3,4-F₂ | (k) |
| 284 | 3,4-Cl₂ | |
| 285 | 3,4-(CH₃O)₂ | |
| 286 | 2,6-Br₂-4-CH₃ | |
| 287 | 2,6-Br₂-4-NH₂ | |
| 288 | 2,4-Cl₂-6-NH₂ | |
| 289 | 2,4-Cl₂ | |
| 290 | 3,5-Cl₂ | |
| 291 | 3-(C₂H₅)₂N | |
| 292 | 2,4-F₂ | |
| 293 | 2,3-F₂ | |
| 294 | 2,3-(CH₃O)₂ | |
| 295 | 3,4-(CH₃)₂ | |
| 296 | 2,4-(CH₃)₂ | |
| 297 | 2,4-(NH₂)₂ | |
| 298 | 3-(OC₂H₅)-4-(OCH₃) | |
| 299 | 4-(OCH₃)-3-(OC₂H₅) | |
| 300 | 5-F-2-NH₂ | |
| 301 | 2-CH₃O-4-NH₂ | |
| 302 | 3-CH₃O-4-NH₂ | |
| 303 | 3-4-OCH₂O | |
| 304 | 3-CH₃-4-NH₂ | |
| 305 | 4-CH₃-3-NH₂ | |
| 306 | 2-CH₃-3-NH₂ | |
| 307 | 2-NH₂-3-CH₃ | |
| 308 | F₅ | (l) |
| 309 | Br₅ | |
| 310 | Cl₅ | |
| 311 | 2,3,5,6-F₄ | |
| 312 | 2,3,5,6-Cl₄ | |
| 313 | 2,4,5-F₃ | |
| 314 | 2,3,5-Cl₃ | |
| 315 | 2,4,5-Br₃ | |

TABLE 6-continued

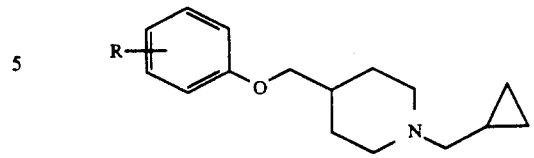

| Ex. | R | mp (°C.) |
|---|---|---|
| 316 | 3,4,5-(CH₃O)₃ | (m) |

Footnotes for Table 6
(a) ¹H-NMR: 7.0–7.0–6.7(m, 4H), 3.7(d, 3H, J=7), 3.05(br d, 2H, J=10), 2.2(d, 2H, J=7), 2.0–1.6(m, 6H), 1.5–1.25(m, 2H), 0.95–0.75(m, 1H), 0.65–0.5(m, 2H), 0.1–0.0(m, 2H), MS: 263.
(b) ¹H-NMR(200MHz, CDCl₃-DMSO): 7.7(d, 2H, J=8), 7.35(d, 2H, J=8), 4.3–4.2(m, 2H), 3.6–3.4(m, 2H), 2.65(d, 2H, J=6), 2.5–2.1(m, 4H), 1.96–1.7(m, 2H), 1.4–1.2(m, 2H), 1.0–0.85(m, 2H), 0.6–0.5(m, 2H); HRMS: Calcd for C₁₆H₂₁ClNO: 279.1390; Found 279.1376.
(c) ¹H-NMR(200MHz, CDCl₃-DMSO): 7.15(s, 4H), 4.25–4.1(m, 2H), 4.2(s, 3H), 3.6–3.4(m, 2H), 2.65(d, 2H, J=7), 2.55–2.1(m, 5H), 1.95–1.75(m, 2H), 1.4–1.25(m, 1H), 1.0–0.85(m, 2H), 0.6–0.45(m, 2H).
(d) Anal.: Calcd for C₁₆H₂₃NO: C, 78.26, H, 9.37, N, 5.71; Found: C, 77.94, H, 9.49, N, 5.55.
(e) Anal.: Calcd for C₂₂H₂₇NO.0.125 H₂O: C, 81.67, H, 8.43, N, 4.33; Found: C, 81.86, 81.85, H, 8.64, 8.71, N, 4.13, 4.05.
(f) Anal.: Calcd for C₁₇H₂₅NO₂.0.3 H₂O: C, 72.72, H, 9.19, N, 4.99; Found: C, 72.98, 73.08, H, 9.04, 9.10, N, 4.97, 4.96.
(g) Anal.: Calcd for C₂₀H₃₁NO: C, 79.73, H, 10.30, N, 4.65; Found: C, 79.71, H, 10.18, N, 4.72.
(h) ¹H-NMR(CDCl₃, 300MHz): 7.15(d, 2H, J=8), 6.75(d, 2H, J=8), 3.7(d, 2H, J=7), 3.05(br d, 2H, J=9), 2.25(s, 3H), 2.15(d, 2H, J=7), 2.0–1.6(m, 5H), 1.45–1.3(m, 2H), 0.9–0.7(m, 1H), 0.5–0.35(m, 2H), 0.1–0.0(m, 2H); HRMS: Calcd for C₁₇H₂₅NOS: 291.1657; Found: 291.1653.
(i) Anal.: Calcd for C₁₈H₂₇NO₂: C, 74.96, H, 9.09, N, 4.85; Found: C, 74.77, H, 9.38, N, 4.75.
(j) ¹H-NMR(CDCl₃, 300MHz): 7.15(d, 2H, J=8), 6.8(d, 2H, J=8), 3.75(d, 2H, J=7), 2.9(br d, 2H, J=10), 2.1(d, 2H, J=7), 1.9–1.5(m, 6H), 1.3–1.1(m, 3H), 0.85–0.7(m, 1H), 0.55–0.45(m, 2H), 0.1–0.0(m, 2H).
(k) ¹H-NMR(CDCl₃, 300MHz): 6.95(q, 1H, J=8), 6.65–6.5(m, 1H), 6.5–6.4(m, 1H), 3.65(d, 2H, J=7), 3.05(br d, 2H, J=10), 2.2(d, 2H, J=7), 2.0–1.8(m, 2H), 1.8–1.6(m, 3H), 1.5–1.3(m, 2H), 0.9–0.7(m, 1H), 0.65–0.5(m, 2H), 0.10–0.0(m, 2H); MS: 281.
(l) ¹H-NMR(CDCl₃): 6.15(s, 2H), 3.85(s, 6H), 3.8(s, 2H), 3.75(d, 3H, J=7), 3.15(br d, 2H, J=10), 2.3(d, 2H, J=7), 2.1–1.7(m, 5H), 1.65–1.4(m, 2H), 1.0–0.8(m, 1H), 0.6–0.45(m, 2H), 0.15–0.05(m, 2H), HRMS: Calcd for C₁₉H₂₉NO₄: 335.2096; Found: 335.2105.
(m) ¹H-NMR(CDCl₃, 200MHz): 4.0(d, 2H, J=7), 3.15(br d, 2H, J=10), 2.3(d, 2H, J=7), 2.05(br t, 2H, J=7)1.9–1.7(m, 3H), 1.5–1.35(m, 2H), 0.95–0.85(m, 1H), 0.55–0.45(m, 2H), 0.15–0.05(m, 2H); HRMS: Calcd for C₁₆H₁₈F₅NO: 335.1308; Found: 335.1304.

TABLE 7

| Ex. | Ar | mp (°C.) |
|---|---|---|
| 317 | 2-naphthyl | 69–71 (a) |
| 318 | 1-naphthyl | |
| 319 | 2-4-dichloro-1-naphthyl | |
| 320 | 4-indolyl | |
| 321 | 5-indolyl | |
| 322 | 5-isoquinolinyl | |
| 323 | 4-pyridyl | 53–54 (b) |
| 324 | 3-pyridyl | |
| 325 | 2-methyl-4-quinolinyl | |
| 326 | 4-quinolinyl | 85–86 (c) |
| 327 | 5-quinolinyl | |
| 328 | 5-pyrimidyl | |

Footnotes for Table 7
(a) Anal.: Calcd for C₂₀H₂₅NO.0.25H₂O: C, 80.09, H, 8.58, N, 4.67; Found: C, 80.30, 80.40, H, 8.58, 8.65, N, 4.52, 4.70.
(b) Anal.: Calcd for C₁₅H₂₂N₂O.0.25H₂O: C, 71.82, H, 8.84, N, 11.17; Found: C, 71.84, 71.86, H, 9.07, 9.07, N, 10.98, 11.06.
(c) Anal.: Calcd for C₁₉H₂₄N₂O.0.75H₂O: C, 73.63, H, 8.29, N, 9.03; Found: C, 73.59, 73.86, H, 8.33, 8.33, N, 8.71, 8.77.

TABLE 8

(I) R—[benzene ring]—CH₂—O—CH₂—[piperidine with N—CH₂—cyclopropyl]

Structure: $R$-C$_6$H$_4$-CH$_2$-O-CH$_2$-piperidine-N-CH$_2$-cyclopropyl

| Ex. | R | mp (°C.) |
|---|---|---|
| 329 | 4-F | (a) |
| 330 | 4-Cl | |
| 331 | 4-Br | |
| 332 | 4-I | |
| 333 | H | |
| 334 | 4-CH$_3$O | |
| 335 | 4-C$_2$H$_5$O | |
| 336 | 4-TBDMSO | |
| 337 | 4-NH$_2$ | |
| 338 | 4-(CH$_3$)$_2$N | |
| 339 | 4-NHC$_2$H$_5$ | |
| 340 | 4-CH$_3$ | |
| 341 | 4-C$_2$H$_5$ | |
| 342 | 4-CH$_2$OH | |
| 343 | 4-CH(OH)CH$_3$ | |
| 344 | 4-CF$_3$ | |
| 345 | 4-CH$_2$ | |
| 346 | 4-CH$_2$N(CH$_3$)$_2$ | |
| 347 | 4-SCH$_3$ | |
| 348 | 3-F | |
| 349 | 3-Cl | |
| 350 | 3-Br | |
| 351 | 3-I | |
| 352 | 3-CH$_3$O | |
| 353 | 3-C$_2$H$_5$O | |
| 354 | 3-CH$_2$OH | |
| 355 | 3-CH(OH)CH$_3$ | |
| 356 | 3-CF$_3$ | |
| 357 | 3-CH$_2$NH$_2$ | |
| 358 | 3-CH$_2$N(CH$_3$)$_2$ | |
| 359 | 3-NH$_2$ | |
| 360 | 3-NHC$_2$H$_5$ | |
| 361 | 3-NHCH$_3$ | |
| 362 | 3-(CH$_3$)$_2$N | |
| 363 | 3-SCH$_3$ | |
| 364 | 2-F | |
| 365 | 2-Cl | |
| 366 | 2-Br | |
| 367 | 2-I | |
| 368 | 2-CH$_3$O | |
| 369 | 2-CH$_3$ | |
| 370 | 2-CH$_2$OH | |
| 371 | 2-CF$_3$ | |
| 372 | 2-CH$_2$NH$_2$ | |
| 373 | 2-NH$_2$ | |
| 374 | 3,4-F$_2$ | |
| 375 | 3,4-Cl$_2$ | |
| 376 | 3,4-(CH$_3$O)$_2$ | |
| 377 | 2,4-Cl$_2$ | |
| 378 | 2,4-F$_2$ | |
| 379 | 2,4-(CH$_3$O)$_2$ | |
| 380 | 3,5-F$_2$ | |
| 381 | 3,4-Cl$_2$ | |
| 382 | 3,4-(CH$_3$)$_2$ | |
| 383 | 2,4-(NH$_2$)$_2$ | |
| 384 | 3,4-(NH$_2$)$_2$ | |
| 385 | 4-(CH$_3$O)-3-NH$_2$ | |
| 386 | 3,4-OCH$_2$O | |
| 387 | F$_5$ | |
| 388 | Cl$_5$ | |
| 389 | 3,4,5-(CH$_3$O)$_3$ | |

Footnote for Table 8
(a) bp 115–137° C.(0.3 mm Hg); ¹H-NMR: 7.33–7.06(m, 2H), 7.03–6.97(m, 2H), 4.45(s, 2H), 3.32(d, 2H, J=6); HRMS: Calcd for C$_{17}$H$_{24}$FNO: 277.1842; Found: 277.1829; Anal.: Calcd for C$_{17}$H$_{24}$FNO: C, 73.61, H, 8.72, N, 5.05; Found: C, 72.68, 72.51, H, 9.27, 8.98, N, 4.66, 4.96.

TABLE 9

(I) Ar—CH$_2$—O—CH$_2$—piperidine-N-CH$_2$-cyclopropyl

| Ex. | Ar | mp (°C.) |
|---|---|---|
| 390 | 2-naphthyl | |
| 391 | 1-naphthyl | |
| 392 | 2-quinolinyl | |
| 393 | 4-quinolinyl | |
| 394 | 2-pyridyl | |
| 395 | 3-pyridyl | |
| 396 | 4-pyridyl | |
| 397 | 2-pyrimidyl | |
| 398 | 2-furyl | |
| 399 | 2-thienyl | |

TABLE 10

4-F-C$_6$H$_4$-O-CH$_2$-piperidine-N-CH$_2$-cyclopropyl(R)

| Ex. | R | mp (°C.) |
|---|---|---|
| 400 | 1-CH$_3$ | |
| 401 | 2-CH$_3$ | (a) |
| 402 | 2,2-Cl$_2$-1-CH$_3$ | (b) |
| 403 | 2,2-(CH$_3$)$_2$-3-(CH=C(CH$_3$)$_2$) | |
| 404 | 2,2-(CH$_3$)$_2$-3(CH=CCl$_2$) | |
| 405 | 2,2-Cl$_2$ | |
| 406 | 2-F | |
| 407 | 2-Cl | |
| 408 | 1-OH | |
| 409 | 2,2,3,3-(CH$_3$)$_4$ | |

Footnotes for Table 10
(a) ¹H-NMR(CDCl$_3$, 300MHz): 6.95(t, 2H, J=8), 6.8(dd, 2H, J=8, 6), 3.75(d, 2H, J=7), 3.2-3.0(m, 2H), 2.45(dd, 1H, J=9, 6), 2.15(dd, 1H, J=9, 7), 2.1-1.9(m, 2H), 1.9-1.7(m, 3H), 1.55-1.4(m, 2H), 1.05(d, 3H, J=7), 1.65-1.45(m, 2H), 0.25(t, 2H, J=7); Calcd for C$_{17}$H$_{24}$FNO: 277.1842; Found: 277.1818.
(b) ¹H-NMR(CDCl$_3$, 300MHz): 7.0–6.9(m, 2H), 6.9–6.8(m, 2H), 3.75(d, 2H, J=7), 3.0–2.9(m, 2H), 2.55(dd, 2H, J=12, 6), 2.1–1.95(m, 2H), 1.9–1.7(m, 4H), 1.4(s, 3H), 1.5–1.3(m, 1H), 1.25(s, 2H); HRMS: Calcd for C$_{17}$H$_{22}$FCl$_2$NO: 345.1063; Found: 345.1064.

EXAMPLE 410

1-(Cyclopropylmethyl)-4-(4'-Fluorophenoxymethyl)-piperidine Hydrochloride Salt

A solution of 1-(cyclopropylmethyl)-4-(4'-fluorophenoxymethyl)piperidine (250 mg, 0.95 mmol) in ether (5 mi) was stirred at room temperature. A 1N hydrogen chloride-ether solution (5 mi) was added dropwise. The precipitate was filtered and washed with copious amounts of ether. Drying in vacuo at 60° C. afforded a white powder (200 mg): mp 162°–164° C.; ¹H-NMR (DMSO-d$_6$): 10.6–10.2 (m, 1H), 7.35–6.85 (m 5H), 3.9 (d, 2H, J=7), 3.6–3.4 (m, 1H), 3.35–3.1 (m, 2H), 3.05–2.75 (m, 3H), 2.1–1.5 (m, 4H), 1.2–1.0 (m, 2H), 0.7–0.55 (m, 2H), 0.25–0.1 (m, 2H); Anal.: Calcd for C$_{16}$H$_{23}$FNO.HCl: C, 63.88, H, 8.04, N, 4.66, F, 6.32, Cl, 11.79; Found: C, 64.08, H, 7.84, N, 4.58, F, 6.10, Cl, 11.96.

The compounds of Table 11 can be prepared using the process described in Example 410, employing the appropriate acid.

TABLE 11

R¹—(phenyl)—(CH₂)ₘO—CH₂—(piperidine)—N—CH₂—cyclopropyl · HX  R² on cyclopropyl   (I)

| Ex. | m | R¹ | R² | HX | mp (°C.) |
|---|---|---|---|---|---|
| 410 | 0 | 4-F | H | HCl | 162–164 |
| 411 | 0 | 4-Cl | H | HCl | 145–146 (a) |
| 412 | 0 | 4-CH₃O | H | HCl | 125–127 (b) |
| 413 | 0 | 3,4,5-(CH₃O)₃ | H | HCl | 113–114 (c) |
| 414 | 0 | 4-CH₂OH | H | HCl | |
| 415 | 0 | H | H | HCl | |
| 416 | 1 | F | H | HCl | 123–125 (d) |
| 417 | 1 | 4-CH₃O | H | HCl | |
| 418 | 0 | 3-(CH₃)₂N | H | HCl | |
| 419 | 3 | F | H | HCl | |
| 420 | 0 | 4-CH₃S | H | HCl | 157–158 (e) |
| 421 | 0 | 3,4-F₂ | H | HCl | 151–152 (f) |
| 422 | 0 | 4-EtNH | H | HCl | 130–133 (g) |
| 423 | 0 | F₅ | H | HCl | 173–174 (h) |
| 424 | 0 | 4-F | 2,2-Cl₂-1-CH₃ | maleate | 156–157 (i) |
| 425 | 0 | 4-F | 2-CH₃ | fumarate | 115–117 (j) |

Footnotes for Table 11
(a) Anal.: Calcd for C₁₆H₂₁ClNO.HCl: C, 60.96, H, 7.03, N, 4.44, Cl, 22.49; Found: C, 60.85, H, 7.30, N, 4.43, Cl, 22.53.
(b) Anal.: Calcd for C₁₇H₂₅NO₂.HCl.0.25H₂O: C, 64.54, H, 8.44, N, 4.43, Cl, 11.20; Found: C, 64.53, 64.54, H, 8.43, 8.50, N, 4.32, 4.44, Cl, 11.58, 11.58.
(c) ¹H-NMR(DMSO-d₆): 10.9–10.6(m, 1H), 6.25(s, 2H), 5.5–5.1(m, 2H), 3.9–3.5(m, 5H), 2.75(s, 6H), 3.55(s, 3H), 3.1–2.8(m, 4H), 2.1–1.6(m, 4H), 1.2–1.0(m, 1H), 0.7–0.55(m, 2H), 0.45–0.3(m, 2H); Anal. Calcd for C₁₉H₂₉NO₄.1.3 HCl: C, 59.61, H, 7.97, N, 3.66, Cl, 12.04; Found: C, 59.31, 59.18, H, 8.10, 8.07, N, 3.50, 3.53, Cl, 11.67, 11.64.
(d) Anal.: Calcd for C₁₇H₂₄FNO.HCl: C, 65.06, H, 8.03, N, 4.46; Found: C, 65.16, 64.98, H, 8.18, 8.29, N, 4.29, 4.12.
(e) Anal.: Calcd for C₁₇H₂₅NOS.HCl: C, 62.27, H, 7.68, N, 4.27, S, 9.78, Cl, 10.81; Found: C, 62.30, H, 7.91, N, 4.17, S, 9.59, Cl, 10.83.
(f) Anal.: Calcd for C₁₆H₂₁F₂NO.HCl: C, 60.47, H, 6.66, N, 4.41, F, 11.96, Cl, 11.16; Found: C, 60.43, H, 6.78, N, 4.25, F, 11.98, C, 10.91.
(g) Anal.: Calcd for C₁₈H₂₈N₂O.2HCl.0.5H₂O: C, 58.37, H, 8.44, N, 7.56; Found: C, 58.24, 58.50, H, 9.07, 8.74, N, 7.07, 6.96.
(h) Anal.: Calcd for C₁₆H₁₈F₅NO.HCl: C, 51.69, H, 5.15, N, 3.76, F, 25.55, Cl, 9.54; Found: C, 51.60, H, 5.07, N, 3.97, F, 25.54, Cl, 9.39.
(i) Anal.: Calcd for C₁₇H₂₂FCl₂NO.C₄H₄O₄: C, 54.56, H, 5.66, N, 3.03, Cl, 15.34, F, 4.11; Found C, 54.47, H, 5.67, N, 3.02, Cl, 15.00, F, 4.10.
(j) Anal.: Calcd for C₁₇H₂₄FNO.C₄H₄O₄: C. 61.75, H, 6.91, N, 3.43, F, 4.65; Found: C, 62.28, 62.15, H, 7.03, 7.04, N, 3.40, 3.38, F, 4.24, 4.09.

The compounds of Table 12 can be prepared using the process described in Example 410, employing the appropriate acid.

TABLE 12

Ar—(CH₂)ₘO—CH₂—(piperidine)—N—CH₂—cyclopropyl · HX   (I)

| Ex. | m | Ar | HX | mp (°C.) |
|---|---|---|---|---|
| 426 | 0 | 2-naphthyl | HCl | 206–208 (a) |
| 427 | 0 | 4-pyridyl | HCl | |
| 428 | 0 | 4-quinolinyl | HCl | |

Footnote for Table 12
(a) Anal.: Calcd for C₂₀H₂₅NO.HCl: C, 72.38, H, 7.90, N, 4.22, Cl, 10.68; Found: C, 72.27, H, 8.09, N, 4.14.

Example 429 describes an alternate procedure to prepare the product of Example 1.

EXAMPLE 429

Synthesis of 1-(cyclopropylmethyl)-4-(4'-Fluorophenoxymethyl)piperidine

A. Ethyl 1-(Cyclopropylcarbonyl)piperidine-4-carboxylate (1) A solution of ethyl isonipecotate (65 g, 413 mmol) and pyridine (65.3 g, 66.8 mL, 826 mmol) in ether (500 mL) was stirred at about 0° C. under a nitrogen atmosphere. A solution of cyclopropyl-carboxylic acid chloride (43.2 g, 37.5 mL, 413 mmol) in ether (500 mL) was added dropwise over 30 minutes. The reaction mixture was stirred while warming gradually to room temperature over 21 hours, then it was poured onto water (1 L) and mixed. The layers were separated; the organic layer was washed once with a 1N hydrochloric acid solution (1 L), then twice with a saturated sodium bicarbonate solution (1 L). The organic solution was dried over magnesium sulfate and filtered. Solvent was removed in vacuo to give a clear pale yellow liquid. Vacuum distillation (bp 140°–145° C., 0.4 mm Hg) afforded a clear colorless liquid (45 g, 48% yield): ¹H-NMR: 4.5–4.25 (m, 1H), 4.15 (q, 2H, J=7), 3.35–3.05 (m, 1H), 2.96–2.7 (m, 1H), 2.65–2.45 (m, 1H), 2.0–1.85 (m, 2H), 1.75–1.5 (m, 3H), 1.25 (t, 3H, J=7), 1.0–0.9 (m, 2H), 0.75–0.6 (m, 2H); HRMS: Calcd for C₁₂H₁₉NO₃:225.1365; Found: 225.1365.

(2) Alternatively, this compound can be made as follows: Ethyl isonipecotate (48 mL, 0.31 mole), (bromomethyl)cyclopropane (85%, 50 g, 0.31 mole), and potassium carbonate (48 g, 0.35 mole) were stirred at room temperature in dry ethyl alcohol (500 mL) for 23 hours. The mixture was filtered through Celite®, rinsed with ethyl acetate and concentrated in vacuo. The resulting mixture was diluted with ethyl acetate (1 L), extracted with H₂O (2×250 mL), dried (MgSO₄) and concentrated in vacuo. The crude product was distilled, bp 90°–115° C. at 0.8 mm Hg, to yield the product (33.8 g, 52%) as a colorless oil, which gave ¹H-NMR and MS data as listed above in Example 420 A (1).

B. 1-(Cyclopropylmethyl)-4-hydroxymethyl piperidine (1) A solution of lithium aluminum hydride in tetrahydrofuran (1 M, 54.6 mL, 54.6 mmol) was added to tetrahydrofuran (100 mL) via syringe with stirring under a nitrogen atmosphere. This solution was cooled to 0° to 5° C. A solution of ethyl 1-(cyclopropyl-methyl) piperidine-4-carboxylate (11.5 g, 55 mmol) in tetrahydrofuran (100 mL) was added dropwise over 15 minutes. The reaction mixture was heated to reflux temperature and stirred for 4 hours. The mixture was cooled to ambient temperature and ethyl acetate (100 mL) was added dropwise, followed by water (20 mL). The resulting suspension was filtered through Celite®. The filtrate was concentrated in vacuo. Vacuum distillation (bp 100° C., 0.1 mm Hg) afforded the product (6.15 g) : ¹H-NMR:3.5 (d, 2H, J=7), 3.1 (d, 2H, J=7), 2.4 (d, 2H, J=7), 2.1–1.6 (m, 6H), 1.55–1.45 (m, 3H), 0.95–0.85 (m, 1H), 0.55–0.45 (m, 2H), 0.25–0.15 (m, 2H); HRMS: Calcd for C₁₀H₁₉NO:169.1467; Found: 169.1467.

(2) Alternatively, this compound can be made as follows: Lithium aluminum hydride (8.55 g, 0.225 mole) was added portionwise over 1 hour to a 0° C. solution of the ester from Step A above (47.6 g, 0.225 mole) in dry Et₂O (500 mL). After 1.5 hours, the reaction was carefully quenched with H₂O (100 mL), then filtered through Celite(o and rinsed with Et₂O. The filtrate was diluted to 1 L total volume with Et₂O, and the phases were separated. The organic phase was extracted with brine, dried (MgSO₄), and concentrated in vacuo. The crude product was distilled, bp 108°–127° C. at 1.2 mm Hg, to yield the product as a colorless oil (29.3 g, 77%), which gave ¹H-NMR and MS data as listed above in Example 420 B (1).

C. 1-(Cyclopropylmethyl)-4-(4'-Fluorophenoxymethyl) piperidine

A solution of 4-fluorophenol (4.08 g, 36.4 mmol), 1-(cyclopropylmethyl)-4-hydroxymethyl-piperidine (6.15 g, 36.4 mmol) from Step B (1) or (2), and triphenylphosphine (14.43 g, 55 mmol) in benzene (100 mL) was stirred with ice-water bath cooling. Diethyl azodicarboxylate (9.58 g, 8.7 mL, 55 mmol) was added dropwise via syringe. The reaction mixture was heated to reflux and stirred for about 72 hour. The mixture was cooled to ambient temperature and solvent was removed in vacuo. The residue was dissolved in ethyl acetate (200 mL), and the organic solution was washed twice with water (100 mL) then twice with a 2N sodium hydroxide solution (100 mL). Drying over magnesium sulfate, filtration and removal of solvent in vacuo gave a solid. Column chromatography using a gradient elution system (chloroform:methanol::95:5 to 4:1) afforded the product 740 mg, 8% yield, mp 34°–36° C.) which gave $^1$H-NMR and MS data identical to that for the product from Example 1D.

The compounds of Table 13 may be prepared using the procedure described for Example 429, employing the appropriate phenol.

TABLE 13

(I)

| Ex. | R | mp (°C.) |
|---|---|---|
| 429-C | 4-F | 34–36 |
| 430 | 4-NO$_2$ | 68–70 |
| 431 | 4-CO$_2$CH$_3$ | |
| 432 | 4-CON(CH$_3$)$_2$ | |
| 433 | 4-CN | 109–111 (a) |

Footnote for Table 13
(a) See also Example 515

Example 434 and subsequent examples describe the preparation of additional compounds of formula (I) (where X=CO or CHOH).

EXAMPLE 434

Synthesis of
1-(Cyclopropylmethyl)-4-(2'-(4''-fluorophenyl)-2'-oxo-ethyl)piperidine A. (1) 1-(4'-fluorophenyl)-2-(4''-pyridyl)ethanone A solution of di-isopropylamine (4.44 g, 6.16 mL, 44 mmol) in anhydrous tetrahydrofuran (50 mL) was cooled to about 0° C. with stirring in a flame-dried flask under a nitrogen atmosphere. A solution of n-butyl lithium in hexane (2.5 M, 17.6 mL, 44 mmol) was added dropwise, then the reaction mixture was stirred at about 0° C. for about 15 minutes. A solution of 4-picoline (3.92 g, 40 mmol) in anhydrous tetrahydrofuran (50 mL) was added dropwise, then the reaction mixture was stirred at about 0° C. for about 15 minutes.

A solution of ethyl 4-fluorobenzoate (6.73 g, 5.87 mL, 40 mmol) in tetrahydrofuran (100 mL) was stirred at about 0° C. under a nitrogen atmosphere. The pyridine-methyl lithium solution, prepared above was added dropwise via a canula. The reaction mixture was then stirred while being warmed to ambient temperature for about 3 hours. The reaction mixture was then poured onto a 2N sodium hydroxide solution (200 mL) and extracted with ethyl acetate three times. The combined organic layers were dried over magnesium sulfate, filtered and concentrated in vacuo.

Column chromatography of the residue with ethyl acetate gave the product, a yellow solid (1.0 g, R$_f$=0.2) : mp 90°–93° C.; $^1$H-NMR: 8.65–8.5 (m, 2H) , 8.05 (dd, 2H, J=8,6), 7.25–7.1 (m, 4H), 4.3 (s, 2H); MS:215; IR (KBr): 1684(s), 1596(s), 1505(m), 1417(m).

The column was eluted with ethyl acetate-methanol (4:1) to give, after removal of solvent in vacuo, a glassy solid, 4-fluorophenyl bis-(4-pyridylmethyl) methanol (1.1 g) :mp 35°–36° C.; $^1$H-NMR: 8.2 (d, 4H, J=6), 7.25 (dd, 2H, J=8,6), 7.0 (dd, 2H, J=7), 6.85 (d, 2H, J=6), 3.8–3.6 (m, 1H), 3.2 (q, 4H, J=10); MS:308; IR(KBr):3420 (br, s), 2928 (m), 1603 (s), 1560 (m), 1510 (s), 1419 (s), Anal.: Calcd for C$_{19}$H$_{17}$FNO.0.5.H$_2$O: C, 71.91, H, 5.72, N, 8.83; Found: C, 71.75, 72.00, H, 5.60, 5.64, N, 8.44, 8.61.

Alternatively, Step 434 A(2) may be used to make an appropriate intermediate.

A. (2) 1-(4'-Fluorophenyl)-2-(4'-pyridyl)ethanone

A solution of sodium bis(trimethylsilylamide) in tetrahydrofuran (1 M, 400 mL, 0.4 mol) was cooled to about 0° C. with stirring under a nitrogen atmosphere. A solution of 4-picoline (37.25 g, 38.9 mL, 0.4 mol) in anhydrous tetrahydrofuran (560 mL) was added dropwise over 30 minutes. The reaction mixture was stirred at 0°–10° C. for 30 minutes.

A solution of ethyl 4-fluorobenzoate (33.6 g, 29.3 mL, 0.2 mol) in anhydrous tetrahydrofuran (400 mL) was cooled to about 0° C. with stirring under a nitrogen atmosphere. The above solution of 4-pyridinemethyl sodium was added dropwise via an additional funnel such that the internal temperature did not exceed 15° C. The reaction mixture was then stirred at ambient temperature for about 3 hours. The reaction mixture was poured onto water (1 L) and extracted three times with ethyl acetate. The combined organic layers were dried over sodium sulfate, filtered and concentrated in vacuo. Vacuum distillation (bp 140° C., 0.1 mm Hg) gave the product (25.3 g), which solidified on cooling and which was identical in all respects to the product from Example 434 A(1).

B.
1-(Cyclopropylmethyl)-4-(2'-(4''-fluorophenyl)-2'-oxo-ethyl)pyridinium bromide A mixture of 1-(4'-fluorophenyl)-2-(4'-pyridyl)ethanone from Step A(1) or A(2) above (5 g, 23.3 mmol) and bromomethyl cyclopropane (18.8 g, 13.5 mL, 140 mmol) was stirred at reflux temperature under a nitrogen atmosphere for about 1 hour. A pale yellow solid formed upon cooling to ambient temperature. Filtration and trituration with copious amounts of ether afforded a pale yellow solid:$^1$H-NMR: 9.45 (d, 2H, J=6), 8.35–8.0 (m, 4H), 7.2 (br t, 2H, J=7), 5.0–4.8 (m, 4H), 1.65–1.4 (m, 1H) , 0. 85–0. 65 (m, 4H)

C.
1-(Cyclopropylmethyl)-4-(2'-(4''-fluorophenyl)-2'-oxo-ethyl)piperidine

Platinum dioxide (1 g) was suspended in degassed ethanol (100 mL) and this suspension was stirred under a hydrogen atmosphere until hydrogen uptake ceased. A solution of 1-(Cyclopropylmethyl)-4-(2'-(4''-fluorophenyl)-2'-oxoethyl)pyridinium bromide from Step B above, (7.9 g) in degassed ethanol (200 mL) was added and the mixture was stirred under a hydrogen atmosphere. After the theoretical amount of hydrogen had been taken up, the suspension was filtered through Celite ®. Solvent was removed in vacuo to give the product as its hydrobromide salt, a white solid.

This solid was dissolved in water; the solution was basified with a 2N sodium hydroxide solution, then extracted with chloroform three times. The combined organic layers were dried over magnesium sulfate and filtered. Solvent was removed in vacuo. Column chromatography (chloroform:methanol::9:1) gave the product, a pale yellow solid ($R_f$=0.25, 2.83 g): mp 73°-75° C.; IR (KBr) : 3072 (w) , 3006 (w) , 2995 (w) , 2943 (s) , 2903 (s), 2840 (w), 2806 (w), 1679 (s), 1594 (s), 1504 (s), 1462 (s), 1448 (w), 1427 (w), 1410 (s); $^1$H-NMR: 8.0 (dd, 2H, J=8,6), 7.15 (br t, 2H, J=8), 3.1 (br d, 2H, J=9), 2.9 (d, 2H, J=7), 2.35 (d, 2H, J=7), 2.1-1.6 (m, 6H), 1.55-1.35 (m, 2H), 1.0-0.8 (m, 1H), 0.65-0.4 (m, 2H), 0.25-0.0 (m, 2H); MS:275; Anal.: Calcd for $C_{17}H_{22}FNO \cdot 0.25 H_2O$: C, 72.96, H, 8.10, N, 5.00, F, 6.78; Found: C, 73.16, 72.99, H, 8.10, 8.06, N, 5.11, 5.13, F, 6.58, 6.52.

The compounds of Table 14 may be prepared using, in sequence, the procedures described in Examples 434 A(1) or A(2), B and C starting with the appropriate benzoate ester.

TABLE 14

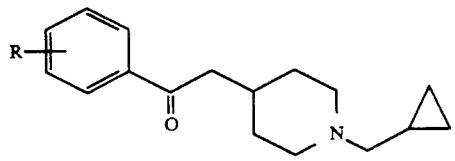

| Ex. | R | Salt | mp (°C.) |
|---|---|---|---|
| 434 | 4-F | | 73-75 |
| 435 | 4-Cl | HBr | 154-155 (a) |
| 436 | 4-Br | | |
| 437 | 4-I | | |
| 438 | H | | |
| 439 | 4-N(CH$_3$)$_2$ | | 104-106 (b) |
| 440 | 4-NHCOCH$_3$ | | |
| 441 | 4-NH$_2$ | | |
| 442 | 4-OCH$_3$ | HBr | 167-168 (c) |
| 443 | 4-OTBDMS | | (d) |
| 444 | 4-OC$_2$H$_5$ | | |
| 445 | 4-SCH$_3$ | | |
| 446 | 4-SC$_2$H$_5$ | | |
| 447 | 4-CH$_2$NH$_2$ | | |
| 448 | 3,5-(CF$_3$)$_2$ | | |
| 449 | 4-CH$_3$ | | |
| 450 | 4-C$_2$H$_5$ | | |
| 451 | 4-CF$_3$ | | 35-36 (e) |
| 452 | 3-Cl | | |
| 453 | 2-Cl | | |
| 454 | 3-Br | | |
| 455 | 2-Br | | |
| 456 | 3-I | | |
| 457 | 2-I | | |
| 458 | 3-N(CH$_3$)$_2$ | | |
| 459 | 3-NHCOCH$_3$ | | |
| 460 | 3-NH$_2$ | | |
| 461 | 3-OCH$_3$ | | |
| 462 | 3-OTBDMS | | |
| 463 | 3-OC$_2$H$_5$ | | |
| 464 | 3-SCH$_3$ | | |
| 465 | 3-CH$_2$NH$_2$ | | |
| 466 | 3-CH$_2$N(CH$_3$)$_2$ | | |
| 467 | 3-CF$_3$ | | |
| 468 | 2-Cl-5-Br | | |
| 469 | 3-Br-4-CH$_3$ | | |
| 470 | 4-t-C$_4$H$_9$O | | |

TABLE 14-continued

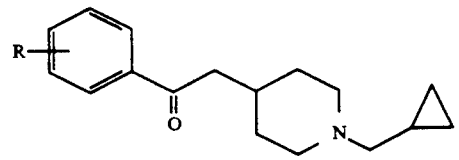

| Ex. | R | Salt | mp (°C.) |
|---|---|---|---|
| 471 | 4-t-C$_4$H$_9$ | HBr | 142-144 (f) |
| 472 | 2-Cl-4-F | | |
| 473 | 3-Cl-4-F | | |
| 474 | 3-Cl-4-OTBDMS | | |
| 475 | 4-Cl-2-OCH$_3$ | | |
| 476 | 3-Cl-4-CH$_3$ | | |
| 477 | 2-Cl-5-(CH$_3$S) | | |
| 478 | 2-Cl-4-(NH$_2$) | | |
| 479 | 4-Cl-3-NH$_2$ | | |
| 480 | 3,5-Br$_2$-4-OTBDMS | | |
| 481 | 3,4-Cl$_2$ | | |
| 482 | 2,4-Cl$_2$ | | |
| 483 | 3,5-Cl$_2$ | | |
| 484 | 2,5-Cl$_2$ | | |
| 485 | 3,5-Cl$_2$-4-OTBDMS | | |
| 486 | 3,4-(OC$_2$H$_5$)$_2$ | | |
| 487 | 3,4-(OCH$_3$)$_2$ | | |
| 488 | 3,4-(OCH$_3$)$_2$ | | |
| 489 | 4-(C$_2$H$_5$)$_2$N | | |
| 490 | 3,4-F$_2$ | | |
| 491 | 2,4-F$_2$ | | |
| 492 | 3,5-F$_2$ | | |
| 493 | 3,4-(CH$_3$)$_2$ | | |
| 494 | 3,5-(CH$_3$)$_2$ | | |
| 495 | 3,5-(NH$_2$)$_2$ | | |
| 496 | 3-CH$_3$O-4-NH$_2$ | | |
| 497 | F$_5$ | | |
| 498 | Cl$_5$ | | |
| 499 | 2,3,4,5-F$_4$ | | |
| 500 | 2,3,5-Cl$_2$ | | |
| 501 | 2,3,4-F$_3$ | | |
| 502 | 2,4,5-F$_3$ | | |
| 503 | 4-C$_6$H$_5$ | HBr | 233-234 (g) |

Footnotes for Table 14

(a) $^1$H-NMR(CDCl$_3$, 300 MHz): 7.88(d, 2H, J=8), 7.45(d, 2H, J=8), 3.77-3.68(m, 2H), 3.02(d, 2H, J=7), 2.90(d, 2H, J=8), 2.85-2.71(m, 2H), 2.40-1.97(m, 5H), 1.59(br m, 1H), 1.40-1.30(m, 1H), 0.85-0.78(m, 2H), 0.48-0.40(m, 2H); Anal.: Calcd for C$_{17}$H$_{22}$ClNO.HBr: C, 54.78, H, 6.22, N, 3.76; Found: C, 54.50, H, 6.21, N, 3.85.

(b) $^1$H-NMR(CDCl$_3$, 300 MHz): 7.9(d, 2H, J=9), 6.65(d, 2H, J=9), 3.2(br d, 2H, J=11), 3.1(s, 6H), 2.85(d, 2H, J=7), 2.4(d, 2H, J=7), 2.3-1.95(m, 4H), 1.9-1.7(m, 2H), 1.7-1.45(m, 2H), 1.1-0.9(m, 1H), 0.7-0.6(m, 2H), 0.3-0.1(m, 2H); HRMS: Calcd for C$_{19}$H$_{28}$N$_2$O: 300.2202; Found: 300.2218; Anal.: Calcd for C$_{19}$H$_{28}$N$_2$O.0.5.H$_2$O: C, 73.75, H, 9.28, N, 9.05; Found: C, 73.22, H, 9.05, N, 8.87.

(c) $^1$H-NMR(CDCl$_3$, 300 MHz): 7.91(d, 2H, J=8), 6.94(d, 2H, J=8), 3.91(s, 3H), 3.76-3.68(m, 2H), 2.95(d, 2H, J=7), 2.90(d, 2H, J=7), 2.85-2.75(m, 2H), 2.40-2.15(m, 3H), 2.05-1.95(m, 2H), 1.60(br m, 1H), 1.40-1.31(m, 1H), 0.84-0.77(m, 2H), 0.50-0.43(m, 2H); Anal.: Calcd for C$_{18}$H$_{25}$NO$_2$.HBr: C, 58.70, H, 7.12, N, 3.80; Found: C, 58.75, 58.54, H, 7.19, 7.14, N, 3.81, 3.81.

(d) $^1$H-NMR(CDCl$_3$, 300 MHz): 7.85(br d, 2H, J=8), 6.85(br d, 2H, J=8), 3.05(br d, 2H, J=10), 2.85(d, 2H, J=7), 2.25(d, 2H, J=7), 2.1(br t, 3H, J=7), 1.85-1.7(m, 2H), 1.5-1.3(m, 2H), 1.0(s, 9H), 0.95-0.8(m, 2H), 0.55-0.45(m, 2H), 0.25(s, 6H), 0.15-0.05(m, 2H); HRMS: Calcd for C$_{23}$H$_{37}$NO$_2$Si: 387.2594; Found: 387.2591.

(e) $^1$H-NMR(CDCl$_3$, 300 MHz): 8.05(d, 2H, J=8), 7.75(d, 2H, J=8), 3.1(br d, 2H, J=10), 2.95(d, 2H, J=7), 2.3(d, 2H, J=7), 2.2-1.95(m, 3H), 1.9-1.7(m, 2H), 2.6-2.35(m, 2H), 1.0-0.8(m, 1H), 0.6-0.45(m, 2H), 0.2-0.05(m, 2H), HRMS: Calcd for C$_{18}$H$_{22}$F$_3$NO: 325.1676; Found: 325.1652; Anal.: Calcd for C$_{18}$H$_{22}$F$_3$NO.0.25.H$_2$O: C, 65.54, H, 6.87, N, 4.24, F, 17.27; Found: C, 65.57, 65.52, H, 6.89, 6.89, N, 4.31, 4.36, F, 17.34.

(f) $^1$H-NMR(CDCl$_3$, 300 MHz): 7.89(d, 2H, J=8), 7.49(d, 2H, J=8), 3.77-3.69(m, 2H), 3.02(d, 2H, J=6), 2.90(d, 2H, J=8), 2.84-1.30(m, 9H), 1.35(s, 9H), 0.85-0.78(m, 2H), 0.48-0.41(m, 2H), HRMS: Calcd for C$_{21}$H$_{21}$NO: 313.2406; Found: 313.2405; Anal.: Calcd for C$_{21}$H$_{31}$NO.HBr.0.5 H$_2$O: C, 62.52, H, 8.25, N, 3.47; Found: C, 62.70, 62.47, H, 8.00, 7.94, H, 3.34, 3.33.

(g) $^1$H-NMR(CDCl$_3$, 300 MHz): 8.03(d, 2H, J=8), 7.70(d, 2H, J=8), 7.65-7.40(m, 5H), 3.78-3.69(m, 2H), 3.08(d, 2H, J=7), 2.90(d, 2H, J=8), 2.87-2.75(m, 2H), 2.43-1.98(m, 5H), 1.58(br m, 1H), 1.43-1.32(m, 1H), 0.95-0.87(m, 2H), 0.49-0.41(m, 2H); Anal.: Calcd for C$_{23}$H$_{25}$NO.HBr: C, 66.66, H, 6.81, N, 3.38; Found: C, 66.23, 66.22, H, 6.86, N, 7.08; N, 3.41, 3.42.

EXAMPLE 504

1-(Cyclopropylmethyl)-4-2'-(4''-Fluorophenyl)-2-oxoethyl)-piperidine, hydrobromide salt A mixture of 1-(cyclopropylmethyl)-4-(2'-(4''-fluorophenyl)-2-oxoethyl)piperidine (24.1 g, 87.6 mmol), a hydrobromic acid solution (0.4 M, 62 ml) and ethanol (50 mL) was stirred with gentle heating until all solid dissolved. Solvent was removed in vacuo with gentle heating to give a white solid. The solid was suspended in a 2-propanol and mixed; again solvent was removed in vacuo with gentle heating to give a white solid. Trituration with ether and filtration gave the product. Drying in vacuo at about 60° C. in a drying oven gave a white powder. (25.9 g): mp 141°–143° C.; IR (KBr) 3067 (w), 3038 (w), 2986 (m), 2939 (s), 2921 (s), 2702 (s), 2645 (s), 2592 (s), 2567 (s), 2520 (s), 1683 (s), 1601 (s), 1509 (s), 1470 (m), 1459 (s), 1436 (s), 1412 (s); $^1$H-NMR (DMSO-d$_6$): 9.5–9.2 (m, 1H), 8.2–8.0 (br t, 2H, J=7), 7.4 (br t, 2H, J=7), 3.6–2.8 (m, 8H), 2.25–1.4 (m, 4H), 1.25–1.0 (m, 1H), 0.7–0.5 (m, 2H), 0.45–0.3 (m, 2H); Anal.: Calcd for C$_{17}$H$_{22}$FNO.HBr: C, 57.31, H, 6.51, N, 3.93, F, 5.33, Br, 22.43; Found: C, 57.57, H, 6.65, N, 3.86, F, 5.15, Br, 22.16.

The compounds of Table 15 may be prepared by the procedure for Example 504 using the appropriate acid.

TABLE 15

(I)

| Ex. | R | Salt | mp (°C.) |
|---|---|---|---|
| 504 | 4F | HBr | 141–143 |
| 505 | 4-CF$_3$ | HCl | 140–142 (a) |
| 506 | 4-N(CH$_3$)$_2$ | HBr | 113–115 (b) |

Footnotes for Table 15
(a) Anal.: Calcd for C$_{18}$H$_{22}$F$_3$NO.HCl.0.5H$_2$O: C, 58.29, H, 6.52, N, 3.77, F, 15.27, Cl, 9.56; Found: C, 58.49, 58.22, H, 6.34, 6.33, N, 3.84, 3.80, F, 15.24, 15.32, Cl, 9.50, 9.28.
(b) Anal.: Calcd for C$_{19}$H$_{28}$N$_2$O.2HBr.0.5H$_2$O: C, 48.42, H, 6.63, N, 5.94, Br, 33.91; Found: C, 48.83, 48.73, H, 6.89, 6.76, N, 5.65, 5.44, Br, 33.10, 33.27.

EXAMPLE 507

1-(Cyclopropylmethyl)-4-(2'-(4''-hydroxyphenyl)-2'-oxoethyl)piperidine, hydrochloride salt 1-(Cyclopropylmethyl)-4-(2'-(4''-t-butyldimethylsilyloxyphenyl)-2'-oxoethyl)piperidine (from Example 443 above) (250 mg, 1.02 mmol) was reacted with a solution of tetra-n-butylammonium fluoride in tetrahydrofuran (1 M, 3 mL, 3 mmol) for about 14.5 hours. Solvent was removed in vacuo. The residue was dissolved in water; a 1N hydrochloric acid solution was added until pH=7. Three extractions with ethyl acetate, drying over magnesium sulfate, filtration and concentration in vacuo gave a light brown oil.

The oil was dissolved in ether-ethanol (5 mL, 1:1 (v/v)). A solution of hydrogen chloride in ether (1 M, 5 mL, 5 mmol) was added with stirring. Solvent was removed in vacuo; the residue was triturated with acetone and filtered. Drying in vacuo gave a white solid (25 mg) : mp 209°–211° C.; NMR (DMSO-d$_6$, 300 MHz) 10.4 (s, 1H), 7.9 (d, 2H, J=8), 6.85 (d, 2H, J=B), 3.55–3.45 (m, 1H), 3.0–2.8 (m, 1H), 1.95–1.85 (m, 2H), 1.7–1.5 (m, 2H), 1.15–1.0 (m, 1H), 0.7–0.6 (m, 2H), 0.45–0.35 (m, 2H); HRMS: Calcd for C$_{17}$H$_{23}$NO$_2$:273.1729; Found: 273.1727.

EXAMPLE 508

1-(Cyclopropylmethyl)-4-(4'-cyanophenoxymethyl)-piperidine

Sodium hydride (50% in oil, 0.48 g, 10 mmol) was washed with hexanes twice (decanting the solvent each time) and suspended in N,N-dimethylformamide (20 mL) with stirring under a nitrogen atmosphere. A solution of 1-(cyclopropylmethyl)-4-(hydroxy-methyl)-piperidine (Example 429B) (1.6 g, 9.5 mmol) in N,N-dimethylformamide (10 mL) was added dropwise. Gas evolution occurred. 4-Fluorobenzonitrile (1.21 g, 10 mmol) was added, then the reaction mixture was stirred at 100° C. for 17 hours. Water was added. The solvent was distilled in vacuo. The residue was taken up in water, basified with a 1N sodium hydroxide solution and extracted three times with ethyl acetate. The combined organic layers were dried over MgSO$_4$ and filtered. Solvent was removed in vacuo to give a brown oil.

Column chromatography (chloroform: methanol::9:1) gave a brown oil, after removal of solvent in vacuo. The oil was crystallized from ether-hexanes and filtered. Drying in vacuo afforded the product, a white powder (1.23 g) : mp 109°–111° C.; IR (KBr) 3074 (w), 2997 (m), 2962 (w), 2939 (s), 2918 (s), 2883 (s), 2826 (s), 2779 (m), 2232 (s), 1607 (s), 1574 (m), 1511 (s); NMR CDCl$_3$, 300 MHz): 7.75 (d, 2H, J=8), 6.9 (d, 2H, J=8), 3.85 (d, 2H, J=7), 3.1 (br d, 2H, J=10), 2.25 (d, 2H, J=7), 2.0 (td, 2H, J=8), 1.9–1.75 (m, 3H), 1.5–1.35 (m, 2H), 0.9–0.8 (m, 1H), 0.55–0.45 (m 2, H), 0.15–0.05 (m, 2H); HRMS: Calcd for C$_{17}$H$_{22}$N$_2$O: 270.1732; Found: 270.1727; Anal.: Calcd for C$_{17}$H$_{22}$N$_2$O: C, 75.52, H, 8.20, N, 10.36; Found: C, 75.36, H, 8.35, N, 10.27.

The compounds in Table 16 may be prepared by the method described in Examples 1, 429 or 508 using the appropriate benzene derivative.

TABLE 16

(I)

| Ex. | R | X | p | Salt | mp (°C.) |
|---|---|---|---|---|---|
| 509 | 4-F | S | 1 | | (a) |
| 510 | 4-F | NMe | 1 | | |
| 511 | 4-F | CHOH | 1 | | 114–116 (b) |
| 512 | 4-NO$_2$ | O | 1 | | 68–70 (c) |
| 513 | 4-F | NH | 1 | | |
| 514 | 1-tetrazole | O | 1 | | |
| 515 | 4-CN | O | 1 | | 109–111 (d) |
| 516 | 4-COCH$_3$ | O | 1 | | 41–43 (e) |
| 517 | 4-SO$_2$(OCH$_2$C$_6$H$_5$) | O | 1 | | |
| 518 | 4-CO$_2$CH$_2$Ph | O | 1 | | |
| 519 | 4-CHO | O | 1 | | |
| 520 | 4-SO$_2$N(CH$_3$)$_2$ | O | 1 | | 118–119 (f) |
| 521 | 4-F | O | 3 | | |
| 522 | 4-F | C=O | 0 | | |
| 523 | 4-F | SO | 1 | | (g) |
| 524 | 4-F | SO$_2$ | 1 | | 73 (h) |
| 525 | 4-F | C=O | 2 | HBr | 108–109 (i) |
| 526 | 4-F | O | 2 | | (j) |

TABLE 16-continued (I)

| Ex. | R | X | p | Salt | mp (°C.) |
|---|---|---|---|---|---|
| 527 | 4-F | O | 2 | fumarate | 124–126 (k) |

Footnotes for Table 16

(a) $^1$H-NMR(CDCl$_3$, 200 MHz): 7.3(dd, 2H, J=8, 6), 7.0(t, 2H, J=8), 3.1(br d, 2H, J=10), 2.8(d, 2H, J=7), 2.15(d, 2H, J=7), 2.0–1.8(m, 4H), 1.6–1.3(m, 3H), 0.95–0.8(m, 1H), 0.6–0.45(m, 2H), 0.15–0.05(m, 2H); HRMS: Calcd for C$_{16}$H$_{22}$FNS: 279.1457; Found: 279.1460.

(b) Anal.: Calcd for C$_{17}$H$_{24}$FNO: C, 73.61, H, 8.72, N, 5.05, F, 6.84; Found: C, 72.64, 72.96, H, 8.77, 8.61, N, 5.00, 4.92, F, 6.86.

(c) Anal.: Calcd for C$_{16}$H$_{22}$N$_2$O$_3$.0.75H$_2$O: C, 63.26, H, 7.74, N, 9.22; Found: C, 63.14, 63.10, H, 7.40, 7.39, N, 9.35, 9.28.

(d) Anal.: Calcd for C$_{17}$H$_{24}$N$_2$O: C, 75.52, H, 8.20, N, 10.36; Found: C, 75.36 H, 8.35, N, 10.27. (See also Example 433).

(e) Anal.: Calcd for C$_{18}$H$_{25}$NO$_2$: C, 75.23, H, 8.77, N, 4.87; Found: C, 75.10, H, 8.87, N, 4.76.

(f) Anal.: Calcd for C$_{18}$H$_{22}$NO$_3$S: C, 61.33, H, 8.01, N, 7.95, S, 9.10; Found: C, 60.64, 60.64, H, 7.98, 7.94, N, 7.63, 7.64, S, 9.03.

(g) Anal.: Calcd for C$_{16}$H$_{22}$FNO$_2$S: C, 61.71, H, 7.12, N, 4.49, F, 6.10, S, 10.30; Found: C, 61.57, H, 7.26, N, 4.39, F, 6.40, S, 10.36.

(h) $^1$H-NMR(CDCl$_3$, 200 MHz): 7.65(dd, 2H, J=7, 2), 7.25(dd, 2H, J=8, 2), 3.1(br t, 2H, J=9), 2.85(dd, 1H, J=10, 2), 2.5(dd, 1H, J=10, 8), 2.4–2.2(m, 2H), 2.15–1.9(m, 5H), 1.8–1.7(m, 1H), 1.55–1.4(m, 2H), 0.9–0.8(m, 1H); 0.6–0.45(m, 2H), 0.15–0.05(m, 2H); HRMS: Calcd for C$_{16}$H$_{22}$FNOS: 295.1406; Found: 295.1409.

(i) Anal.: Calcd for C$_{18}$H$_{24}$FNO.HBR: C, 58.38, H, 6.53, N, 3.78, F, 5.13, Br, 21.57; C, 58.13, 58.35, H, 6.51, 6.38, N, 3.70, 3.61, F, 4.95, 4.93, Br, 21.59.

(j) $^1$H-NMR(CDCl$_3$, 300 MHz): 6.9(br t, 2H, J=8), 6.75(dd, 2H, J=8, 6), 3.7(d, 2H, J=7), 2.9(br d, 2H, J=9), 2.5–2.35(m, 2H), 2.0–1.85(m, 2H), 1.85–1.65(m, 3H), 1.5–1.3(m, 4H), 0.7–0.5(m, 1H), 0.45–0.3(m, 2H); 0.1–0.0(m, 2H); HRMS: Calcd for C$_{17}$H$_{24}$FNO: 277.1842; Found: 277.1837.

(k) Anal.: Calcd for C$_{17}$H$_{24}$FNO.C$_4$H$_4$O$_4$: C, 64.11, H, 7.17, N, 3.56, F, 4.82; Found: C, 64.05, 64.30, H, 7.30, 7.41, N, 3.89, 3.90, F, 4.83, 4.85.

The compounds in Table 17 may be prepared by the method described in Example 1C using the appropriate hydroxy aromatic compound.

TABLE 17

(I)

| Ex. | R | X | n | mp (°C.) |
|---|---|---|---|---|
| 528 | 4-piperidinyl | O | 1 | |
| 529 | 4-C$_6$H$_5$ | O | 1 | |
| 530 | 4-C$_6$H$_5$O | O | 1 | 62–63 (a) |
| 531 | 4-C$_6$H$_5$S | O | 1 | |
| 532 | 4-(4'-FC$_6$H$_4$) | O | 1 | 81–83 (b) |
| 533 | 4-(4'-CH$_3$OC$_6$H$_4$) | O | 1 | 122–123 (c) |
| 534 | 4-(4'-CH$_3$C$_6$H$_4$) | O | 1 | |
| 535 | 4-(4'-CH$_3$SC$_6$H$_4$) | O | 1 | |
| 536 | 4-(4'-CF$_3$C$_6$H$_4$) | O | 1 | |
| 537 | 4-F | O | 0 | |

Footnotes for Table 17

(a) Anal.: Calcd for C$_{22}$H$_{27}$NO$_2$: C, 78.30, H, 8.06, N, 4.15; Found: C, 78.20, H, 8.12, N, 4.04.

(b) Anal.: Calcd for C$_{22}$H$_{26}$FNO: C, 77.84, H, 7.72, N, 4.13, F, 5.60; Found: C, 77.71, 77.71, H, 7.78, 7.78, N, 3.93, 3.93, F, 3.77, 3.60.

(c) Anal.: Calcd for C$_{23}$H$_{29}$NO$_2$.0.5H$_2$O: C, 76.62, H, 8.39, N, 3.88; Found: C, 76.83, 76.86, H, 8.20, 8.17, N, 3.60, 3.58.

The compounds in Table 18 may be prepared by the methods described in Example 508 or 410, using the appropriate starting materials.

TABLE 18

| Ex. | Ar | HX | mp (°C.) |
|---|---|---|---|
| 538 | 2-pyrimidyl | | (a) |
| 539 | 2-pyrimidyl | HCl | 151–152 (b) |
| 540 | 2-pyridyl | | (c) |
| 541 | 2-pyridyl | HCl | 176–178 (d) |

Footnotes for Table 18

(a) $^1$H-NMR(CDCl$_3$, 300 MHz): 8.45–8.35(m, 2H), 6.85–6.8(m, 1H), 4.1(d, 2H, J=7), 3.05(br d, 2H, J=10), 2.2(d, 2H, J=7), 2.0–1.7(m, 5H), 1.45–1.3(m, 2H), 0.9–0.75(m, 2H), 0.1–0.0(m, 2H).

(b) Anal.: Calcd for C$_{14}$H$_{21}$N$_3$O.1.3HCl: C, 57.05, H, 7.62, N, 14.26, Cl, 15.64; Found: C, 56.18, 56.34, H, 7.51, 7.65, N, 13.95, 14.05, Cl, 15.05, 15.25.

(c) $^1$H-NMR(CDCl$_3$, 300 MHz): 8.05–8.0(m, 1H), 7.15–7.35(m, 1H), 6.8–6.7(m, 1H), 6.65–6.55(m, 1H), 4.05(d, 2H, J=7), 3.05(br d, 2H, J=10), 2.2(d, 2H, J=7), 1.9(br t, 2H, J=9), 1.8–1.6(m, 3H), 1.5–1.3(m, 2H), 0.9–0.7(m, 1H), 0.5–0.35(m, 2H), 0.1–0.0(m, 2H); MS: 246.

(d) Anal.: Calcd for C$_{15}$H$_{22}$N$_2$O.1.5HCl: C, 56.52, H, 7.43, N, 8.78, Cl, 16.68; Found: C, 56.37, 56.18, H, 7.77, 7.76, N, 8.61, 8.44, Cl, 19.76, 19.66.

EXAMPLE 542

1-(Cyclopropylmethyl)-4-(2'-(4''-cyanophenyl)-2'-oxoethyl)piperidine

A mixture of sodium cyanide (4.9 g, 100 mmol) and 1-(cyclopropylmethyl)-4-(2'-(4''-fluorophenyl)-2'-oxo ethyl)piperidine (Example 434, 1.0 g, 3.6 mmol) in N,N-dimethylformamide (50 mL) was stirred at 120° C. for 26 h. The excess solvent was distilled in vacuo; the residue was dissolved in water and extracted three times with ethyl acetate. The combined organic layers were washed with water twice, dried over anhydrous magnesium sulfate and filtered. Solvent was removed in vacuo to give an oil.

Column chromatography (CHCl$_3$: MeOH::9:1) afforded the product, a solid (0.68 g. 67% yield): mp 107°–108° C.; Anal.: Calcd for C$_{18}$H$_{22}$N$_2$O.0.25H$_2$O: C, 75.38, H, 7.90, N, 9.76; Found: C, 75.13, 74.97, H, 7.87, 7.96, N, 9.65, 9.52.

EXAMPLE 543

1-(Cyclopropylmethyl)-4-(2'-(4''-aminophenyl)-2'-oxoethyl)piperidine

Following the procedure of Example 542, sodium azide (6.5 g, 100 mmol) was reacted with the product of Example 434 (1.0 g, 3.6 mmol) to afford the title compound, a solid (0.35 g): mp 140–146 (dec); MS:272; Anal.: Calcd for C$_{17}$H$_{22}$N$_2$O.0.75H$_2$O: C, 71.42, H, 8.99, N, 9.80; Found: C, 71.06, 71.03, H, 8.58, 8.54, N, 9.98, 9.99.

EXAMPLE 544

1-(Cyclopropylmethyl)-4-(4'-methylsulfonylphenoxymethyl)piperidine

A mixture of a 1N NAOH solution (10 mL) and 17 (cyclopropylmethyl)-4-(4'-methylthiophenoxymethyl)-piperidine, hydrochloride salt (Example 420, 0.5 g, 1.5 mmol) was stirred for 15 min and then extracted three times with ethyl acetate. The combined organic extracts were dried over anhydrous magnesium sulfate and filtered. Solvent was removed in vacuo. The residue was taken up in a mixture of methanol (10 mL) and water (10 mL). Sodium periodate (2.13 g, 10 mmol) was added; the resulting suspension was stirred for 22 h. The reaction mixture was diluted with 250 mL water, basified with 1N NAOH solution and extracted three times with ethyl acetate. The combined organic layers were dried over magnesium sulfate and filtered. Solvent was removed in vacuo.

Column chromatography (CHCl$_3$:MeOH::9:1) of the residue afforded the title compound, a solid (0.29 g): mp 134°–135° C.; $^1$H-NMR (CDCl$_3$, 300 MHz) : 7.85 (d, 2H, J=8), 7.0 (d, 2H, J=8), 3.9 (d, 2H, J=7), 3.15 (br d, 2H, J=10), 3.05 (s, 3H), 2.3 (d, 2H, J=7), 2.1 (br t, 2H, J=7), 1.95–1.8 (m, 3H), 1.6–1.4 (m, 2H), 0.95–0.85 (m, 1H), 0.6–0.5 (m, 2H), 0.2–0.1 (m, 2H); HRMS: Calcd for C$_{17}$H$_{25}$NO$_3$S: 323.1555; Found: 323.1554.

EXAMPLES 545 AND 546

1-(Cyclopropylmethyl)-4-(4'-fluorophenylsulfonylmethyl)piperidine (Example 545) and 1-(cyclopropylmethyl) -4-(4'-fluorophenyl-sulfinylmethyl) piperidine (Example 546)

1-(Cyclopropylmethyl)-4-(4'-fluorophenylthiomethyl)piperidine, hydrobromide salt (Example 509, hydrobromide salt, 1.0 g) was treated with a 1N NAOH solution (50 mL); the mixture was extracted with ethyl acetate three times. The organic solution was dried over magnesium sulfate and filtered. Solvent was removed in vacuo.

The residue was reacted with sodium periodate (7.7 g, 36 mmol) in methanol (30 mL) and water (30 mL for 21.5 h). The reaction mixture was diluted with water (500 mL), basified with a 1N NAOH solution and extracted three times with ethyl acetate. The combined organic layers were dried over magnesium sulfate and filtered. Solvent was removed in vacuo.

Column chromatography (CHCl$_3$:MeOH::9:1) gave two products:

(1) (Cyclopropylmethyl)-4-(4'-fluorophenylsulfonylmethyl)piperidine (Example 545) R$_f$=0.3, 367 mg): mp 73° C.; $^1$H-NMR (CDCl$_3$, 200 MHz) : 7. 95 (dd, 2H, J=7, 2) , 7.25 (dd, 2H, J=8,2), 3.1–2.95 (m, 2H), 3.05 (d, 2H, J=7), 2.25 (d, 2H, J=7), 2.1–1.85 (m, 4H), 1.55–1.4 (m, 2H), 0.9–0.8 (m, 1H), 0.55–0.45 (m, 2H), 0.15–0.05 (m, 2H); Anal.: Calcd for C$_{16}$H$_{22}$FNO$_2$S: C, 61.71, H, 7.12, N, 4.49, F, 6.10, S, 10.30; Found: C, 61.57, H, 7.26, N, 9.39, F, 6.40, S, 10.36;

(2) 1-(cyclopropylmethyl)-4-(4'-fluorophenylsulfinylmethyl)piperidine (Example 546, R$_f$=0.17, 90 mg): $^1$H-NMR (CDCl$_3$, 200 MHz): 7.65, (dd, 2H, J=7,2), 7.25 (dd, 2H, J=8,2), 3.1 (br t, 2H, J=9), 2.85 (dd, 1H, J=10,2), 2.5 (dd, 1H, J=10,8), 2.4–2.2 (m, 2H), 2.15–1.9 (m, 5H), 1.8–1.7 (m, 1H), 1.55–1.4 (m, 2H), 0.9–0.8 (m, 1H), 0.6–0.45 (m, 2H), 0.15–0.05 (m, 2H); HRMS: Calcd for C$_{16}$H$_{22}$FNOS: 295.1406; Found: 295.1409.

EXAMPLE 547

1-(Cyclopropylmethyl)-4-(2'-(4''-fluorophenyl)-2'-phenyl-2'-hydroxyethyl)piperidine 1-(Cyclopropylmethyl)-4-(2'-(4''-fluorophenyl)-2'-oxoethyl)piperidine (Example 429, 1.0 g, 3.6 mmol) was mixed with dry tetrahydrofuran (10 mL). A solution of phenyl magnesium bromide in ether (3.0 M, 3 mL, 9 mmol) was added with stirring. The reaction mixture was stirred for 24 h; poured onto a saturated NH$_4$Cl solution and extracted with ethyl acetate three times. The combined organic layers were dried over magnesium sulfate and filtered. Solvent was removed in vacuo. Trituration with ether-hexanes (1:9) and filtration afforded the title compound, a solid, which was dried in vacuo (0.9 g). mp 115°–116° C.; Anal. : Calcd for C$_{23}$H$_{28}$FNO: C, 77.36, H, 7.90, N, 3.92, F, 5.32; Found: C, 77.47, 77.41, H, 8.00, 7.92, N, 3.42, 3.52, F, 5.09.

EXAMPLE 548

1-(Cyclopropylmethyl)-4-(2',2'-bis (4''-Fluorophenyl)-2-hydroxyethyl)piperidine

Following the procedure described for Example 547, the compound of Example 429 (1.0 g, 3.6 mmol) was reacted a solution of 4-fluorophenylmagnesium bromide in tetrahydrofuran (1.0 M, 9 mL, 9 mmol) to give the title compound, a solid (1.1 g) : mp 119°–121° C.; Anal. : Calcd for C$_{23}$H$_{27}$F$_2$NO.0.5H$_2$O: C, 72.60, H, 7.41, N, 3.68, F, 9.99; Found: C, 72.89, 72.84, H, 7.14, 7.21, N, 3.29, 3.24, F, 9.82, 9.67.

EXAMPLE 549

1-(Cyclopropylmethyl)-4-(2'-(4''-fluorophenyl)-2'-oxo-1'-benzylethyl)piperidine

A solution of the compound of Example 429 (1.0 g, 3.6 mmol) in dry tetrahydrofuran (25 mL) was stirred at 0° C. A solution of sodium bis(trimethylsilyl)amide in tetrahydrofuran (1 M, 4 mL, 4 mmol) was added and stirring was continued for 40 min. Benzyl chloride (0.51 g, 0.46 mL, 4 mmol) was added; the reaction mixture was heated to reflux temperature and stirred for 23 h. The reaction mixture was cooled to ambient temperature, poured onto water, basified with a 1N NAOH solution and extracted with ethyl acetate three times. The combined organic layers were dried over magnesium sulfate, filtered and concentrated in vacuo. Column chromatography (CHCl$_3$:MeOH::9:1) gave the title compound (455 mg), a yellow oil: $^1$H-NMR (CDCl$_3$, 200 MHz): 7.7 (dd, 2H, J=8,6), 7.2–7.0 (m, 5H), 7.0 (t, 2H, J=8), 3.65–3.55 (m, 1H), 3.2–2.9 (m, 4H), 2.25 (d, 2H, J=7), 2.0–1.7 (m, 4H), 1.65–1.4 (m, 3H), 0.9–0.75 (m, 1H), 0.55–0.45 (m, 2H), 0.15–0.05 (m, 2H); HRMS: Calcd for C$_{24}$H$_{28}$FNO: 365.2155; Found: 365.2156.

EXAMPLE 550

1-(Cyclopropylmethyl)-4-(4'-(5''-tetrazolyl)phenoxymethyl)piperidine

A mixture of 1-(cyclopropylmethyl)-4-(4''-cyanophenoxy)methylpiperidine (Example 515, 0.75 g, 2.8 mmol), sodium azide (0.2 g, 3 mmol), ammonium chloride (0.15 g, 3 mmol) and N,N-dimethylformamide (10 mL) was stirred at 100°–120° C. for 23 h. The excess solvent was distilled in vacuo; the residue was suspended in water. A concentrated hydrochloride solution was added until pH=1. The solid formed was filtered, washed with water and dried in vacuo. The title compound (100 mg) had the following analytical data: $^1$H-NMR (DMSO-d$_6$, 300 MHz): 7.9 (d, 2H, J=7), 7.0 (d, 2H, J=7), 3.95 (d, 2H, J=6), 3.45 (br d, 2H, J=9), 2.9–2.75 (m, 3H), 2.1–1.9 (m, 3H), 1.7–1.5, (m, 2H), 1.1–1.0 (m, 1H), 0.7–0.6 (m, 2H), 0.45–0.3 (m, 2H); MS:313.

EXAMPLE 551

1-(t-Butyldimethylsilyloxy)-4-(4'-methoxyphenyl)benzene

A solution of 4-bromoanisole (1.87 g, 10 mmol) in dry tetrahydrofuran (20 mL) was cooled to −78° C. with stirring under a nitrogen atmosphere. A solution of t-butyl lithium in pentane (1.7 M, 11.8 mL, 20 mmol)

was added dropwise. The reaction mixture was stirred at −78° C. for 1 h. A solution of freshly-fused zinc chloride (2.04 g, 15 mmol) in dry tetrahydrofuran (20 mL) was added; the reaction mixture was warmed to −20° C. over 20 min, then cooled to −78° C. A solution of 1-bromo-4-t-butyl-dimethylsilyloxybenzene (2.86 g, 10 mmol) in dry tetrahydrofuran (10 mL) was added, followed by tetrakis (triphenylphosphine)palladium (0) (1.15 g, 1 mmol). The reaction was warmed to 50° C. and stirred for 21 h. The reaction mixture was poured onto a saturated NH₄Cl solution and extracted three times with ethyl acetate. Drying over magnesium sulfate, filtration and removed in vacuo afforded the crude product.

Column chromatography, first with ethyl acetate-hexanes (1:9), then hexanes, afforded the title compound, a solid (2.2 g): ¹H-NMR (CDCl₃, 300 MHz): 7.45 (d, 2H, J=8), 7.4 (d, 2H, J=8), 6.95 (d, 2H, J=B), 6.9 (d, 2H, J=8), 3.85 (s, 3H), 1.0 (s, 9H), 0.25 (s, 6H). The product was still contaminated with trace amounts of triphenylphosphine and starting silyl ether.

EXAMPLE 552

1-(t-Butyldimethylsilyloxy)-4-(4'-methylthiophenyl)-benzene

Using the procedure described for Example 551, 4-bromothioanisole (2.03 g, 10 mmol) was converted to the title compound, a solid (0.51 g): ¹H-NMR (CDCl₃, 300 MHz): 7.5 (d, 2H, J=8), 7.45 (d, 2H, J=8), 6.9 (d, 2H, J=8), 6.7 (d, 2H, J=8), 2.5 (s, 3H), 1.0 (s, 9H), 0.2 (s, 6H). This product was also contaminated with triphenylphosphine and starting bromide.

EXAMPLE 553

1-(t-Butyldimethylsilyloxy)-4-(4'-fluorophenyl)benzene

Using the procedure described for Example 551, 4-bromofluorobenzene (1.75 g, 10 mmol) was reacted to give the title compound (2.94 g): ¹H-NMR (CDCl₃, 300 MHz): 7.5 (dd, 2H, J=8,6), 7.4 (d, 2H, J=8), 7.1 (br t, 2H, J=8), 6.9 (d, 2H, J=8), 6.7 (d, 2H, J=8), 1.0 (s, 9H), 0.25 (s, 6H). This product was contaminated with triphenylphosphine and starting silyl ether.

EXAMPLE 554

Ethyl-4-(4'-fluorophenyl)benzoate

Using the procedure of Example 551, 4-bromofluorobenzene (1.75 g, 10 mmol) was metallated and coupled with ethyl 4-bromobenzoate (2.28 g, 10 mmol) to give the title compound after chromatography (ethyl acetate-hexanes (1:9) (0.7 g)): ¹H-NMR (CDCl₃, 300 MHz): 8.1 (d, 2H, J=8), 7.65–7.5 (m, 4H), 7.15 (t, 2H, J=8), 4.4 (q, 2H, J=7), 1.4 (t, 3H, J=7); MS:244.

Examples 555 through 557 were prepared according to the methods described for Example 1A (Table 19).

TABLE 19

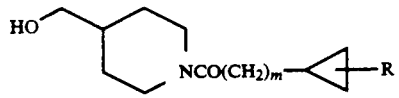

| Ex. | R | m | bp (°C.) |
|---|---|---|---|
| 555 | 2-CH₃ | 0 | 145–150 (0.5 mm Hg) (a) |
| 556 | 2,2-Cl₂-1-CH₃ | 0 | (b) |
| 557 | H | | 1 | 145–150 (0.2 mm Hg) (c) |

Footnotes for Table 19
(a) ¹H-NMR(CDCl₃, 300 MHz): 4.7–4.5(m, 1H), 4.3–4.1(m, 1H), 3.6–3.4(m, 2H), 3.1(br t, 1H, J=7), 2.6(br t, 1H, J=7), 2.0–1.6(m, 5H), 1.5–1.0(m, 4H), 1.1(d, 3H, J=7), 0.65–0.55(m, 1H); MS: 197.
(b) mp=105–107° C.; ¹H-NMR(CDCl₃, 300 MHz): 4.6(br t, 1H, J=7), 3.95(br t, 1H, J=7), 3.6–3.5(m, 2H), 3.25(m, 1H), 2.8–2.6(m, 1H), 2.1–1.7(m, 6H), 1.55(d, 3H, J=7), 1.5–1.1(m, 2H); MS: 265.
(c) ¹H-NMR(CDCl₃, 300 MHz): 4.65(br d, 1H, J=10), 3.9(br d, 1H, J=10), 3.55–3.45(m, 2H), 3.1–2.9(m, 2H), 2.65–2.5(m, 1H), 2.3(d, 2H, J=7), 2.0–1.6(m, 4H), 1.3–1.0(m, 4H).

UTILITIES SECTION

The compounds of this invention and their pharmaceutically acceptable salts possess psychotropic properties, particularly antipsychotic activity of good duration with selective sigma receptor antagonist activities while lacking the typical movement disorder side-effects of standard dopamine receptor antagonist antipsychotic agents. These compounds may also be useful as antidotes for certain psychotomimetic agents such as phencyclidine (PCP), and as antidyskinetic agents.

IN VITRO

Sigma Receptor Binding Assay

Male Hartley guinea pigs (250–300 g, Charles River) were sacrificed by decapitation. Brain membranes were prepared by the method of Tam (Proc. Natl. Acad. Sci. USA 80: 6703–6707, 1983). Whole brains were homogenized (20 seconds) in 10 vol (wt/vol) of ice-cold 0.34 M sucrose with a Brinkmann Polytron (setting 8). The homogenate was centrifuged at 920×g for 10 minutes. The supernatant was centrifuged at 47,000×g for 20 minutes. The resulting membrane pellet was resuspended in 10 vol (original wt/vol) of 50 mM Tris HCl (pH 7.4) and incubated at 37° C. for 45 minutes to degrade and dissociate bound endogenous ligands. The membranes were then centrifuged at 47,000×g for 20 minutes and resuspended in 50 mM Tris HCl (50 mL per brain).

0.5 mL aliquots of the membrane preparation were incubated with unlabeled drugs, 1 nM (+)-[³H] SKF 10,047 in 50 mM Tris HCl, pH 7.4, in a final volume of 1 mL. Nonspecific binding was measured in the presence of 10 μM (+)-SKF 10,047. The apparent dissociation constant (Kd) for (+)-[³H]SKF 10,047 is 50 nM. After 45 minutes of incubation at room temperature, samples were filtered rapidly through Whatman GF/C glass filters under negative pressure, and washed 3 times with ice-cold Tris buffer (5 mL).

IC₅₀s were calculated from log-logit plots. Apparent K$_i$s were calculated from the equation, $K_i = IC_{50}/[1+(L/K_d)]$ (4), where L is the concentration of radioligand and $K_d$ is its dissociation constant. Data are shown in Table I.

DOPAMINE RECEPTOR BINDING

Membranes were prepared from guinea pig striatum by the method described for sigma receptor binding. The membranes were then resuspended in 50 mM Tris HCl (9 mL per brain).

0.5 mL aliquots of the membrane preparation were incubated with unlabeled drugs, and 0.15 nM [³H]spiperone in a final volume of 1 mL containing 50 mm Tris HCl, 120 MM NaCl and 1 mM MgCl₂ (pH 7.7). Nonspecific binding was measured in the presence of 100 nM (+)-butaclamol. After 15 minutes of incubation at 37° C., samples were filtered rapidly through Whatman GF/C glass filters under negative pressure, and washed three times with ice-cold binding buffer (5 mL).

IC₅₀s were calculated from log-logit plots. Apparent $K_i$s were calculated from the equation $K_i = IC_{50}[1 + (L/K_d)](4)$, where L is the concentration of radioligand and $K_d$ is its dissociation constant. Data are shown in Table I.

The data in Table I indicate that haloperidol, a typical antipsychotic drug, has potent binding affinity for both the sigma and dopamine receptors. This binding profile of haloperidol reflects the therapeutic activity as well as the motor side effects caused by antagonism of the dopamine receptors. In contrast, the examples of this invention shown in Table I indicate potent and selective binding affinity for sigma receptors without binding to the dopamine receptors. Therefore these compounds are not expected to produce the extrapyramidal symptoms that are typical of that produced by haloperidol and other typical antipsychotics that are dopamine receptor antagonists.

IN VIVO

Isolation-Induced Aggression in Mice

This is a modification of the method of Yen et al. (Arch. Int. Pharmacodyn. 123: 179-185, 1959) and Jannsen et al. (J. Pharmacol. Exp. Ther. 129: 471-475, 1960). Male Balb/c mice (Charles River) were used. After 2 weeks of isolation in plastic cages (11.5×5.75×6 in) the mice were selected for aggression by placing a normal group-housed mouse in the cage with the isolate for a maximum of 3 minutes. Isolated mice failing to consistently attack an intruder were eliminated from the colony.

Drug testing was carried out by treating the isolated mice with test drugs or standards. Fifteen minutes after dosing with test drugs by the oral route, one isolated mouse was removed from its home cage and placed in the home cage of another isolate. Scoring was a yes or no response for each pair. A maximum of 3 minutes was allowed for an attack and the pair was separated immediately upon an attack. Selection of home cage and intruder mice was randomized for each test. Mice were treated and tested twice a week with at least a 2 day washout period between treatments.

As shown in Table II, haloperidol and Examples 1, 228, 409, 493 and 494 all have potent activities in inhibiting the isolation-induced aggressive behavior indicating psychotropic activities.

PCP-INDUCED TURNING BEHAVIOR IN RATS

Male Sprague-Dawley rats (CD/CR, Charles River), weighing 190-290 g, were used for surgery. In order to spare nonadrenergic neurons, rats were injected with 25 mg/kg imipramine i.p. 30 minutes before surgery. The rats were anesthetized with a 1:1.2 ratio mixture of Xylazine:Ketamine given 0.1 mL/100 g body weight i.m. A Ringers-Wydaze (100:0.01) solution was given to prevent dehydration. Dopamine was depleted in the right striatum by injecting the neurotoxin 6-hydroxydopamine (6-OHDA) into the substantia nigra of the right cerebral hemisphere. Five mg of 6-OHDA was dissolved in 5 mL of a 0.04% ascorbic acid solution which had been deoxygenated with nitrogen. Five µL of the 6-OHDA solution was injected into the substantia nigra through a 26 gauge needle over a five minute period. Stereotaxic injection coordinates were −2.5 mm posterior to bregma, −2.1 mm right of the midsagittal suture, and −8.6 mm below the skull surface with the incisor bar set at +5.0 mm. Following surgery they were given 10 days to recover while housed four per cage (45.0 L×20.0 H×26.0 W) with ALPHA-dri bedding and ad lib access to Pro-Lab rodent chow and deionized water. Following recovery, the wood clips were removed, the rats were individually housed in suspended cages, and they were placed on a restricted diet so that their weight did not exceed 375 g. At all times they were housed in the animal care facility under a 12—12 hour light/dark cycle (light on at 6:00 h, light off at 18:00 h).

Rotation rate and direction were determined with Coulbourn Instruments Rotometry Monitors. Clockwise and counter clockwise rotations were recorded at 30 and 60 minute intervals. The rats were examined for correct lesion location by testing for rotational activity induced by s.c. injections of 3.0 mg/kg D-amphetamine SO₄, and 2.0 mg/kg PCP HCl, respectively. These drugs were administered in the following sequence: Amphetamine was given 30 second before testing. Seven days later, the rats were injected with PCP 30 seconds before testing. Only those rats with an ipsilateral rotation rate of 2.5 turns per minute or higher were used in subsequent tests.

Methocel ® or test drugs were administered by the oral route (p.o.) 20 minutes before testing. Phencyclidine (1.5 mg/kg) was given s.c. immediately before testing.

The data were analyzed with an analysis of variance statistical test and individual comparisons of each dose of test drug to control were made with Dunnett's multiple range test. The ED50 was calculated with a Litchfield and Wilcoxon test using percent of control values. Data are shown in Table III.

INDUCTION OF CATALEPSY

This is a modification of the method of Costall and Naylor (Psychopharmacologia (Berl.), 43, 69–74, 1975). Male CD rats (Charles River) weighing 250-300 g were treated with test drugs and standards by the oral route and tested for the presence of catalepsy 30 minute, 60 minute, and 90 minute after treatment. To test for catalepsy, each rat is placed with its front paws over a 10 cm high horizontal bar. The intensity of catalepsy is measured by the length of time it takes the animal to move both forelegs to the table. A time of 20 seconds is considered maximal catalepsy. Data is shown in Table III.

As shown in Table III, both haloperidol and Example 494 have potent activity in inhibiting the potent hallucinogen PCP-induced turning behavior in rats, supporting their use for treatment of psychosis. In the catalepsy test which is a model for extrapyramidal symptoms, haloperidol is very potent in producing catalepsy and this agrees well with the side-effect profile of haloperidol in the clinic. In contrast, Example 494 does not produce catalepsy and suggests very low potential for extrapyramidal symptoms and tardive dyskinesia.

TABLE I

| | Receptor Binding Affinity | |
|---|---|---|
| Example | Sigma | (D-2) |
| Haloperidol | +++ | +++ |
| 1 | +++ | − |
| 230 | +++ | − |
| 233 | ++ | − |
| 234 | +++ | − |
| 240 | ++ | − |
| 411 | +++ | − |
| 412 | +++ | − |
| 413 | ++ | − |
| 416 | +++ | − |
| 435 | +++ | − |
| 442 | ++ | − |
| 504 | +++ | − |
| 505 | ++ | − |
| 506 | ++ | − |
| 544 | ++ | − |
| 539 | + | − |
| 541 | ++ | − |
| 542 | +++ | − |
| 543 | + | − |
| 547 | +++ | − |
| 548 | +++ | + |
| 545 | + | − |
| 546 | +++ | − |
| 549 | + | − |
| 420 | +++ | − |
| 421 | +++ | − |
| 422 | ++ | − |
| 423 | +++ | − |
| 323 | + | − |
| 326 | ++ | − |
| 424 | +++ | + |
| 425 | +++ | − |
| 525 | +++ | + |
| 515 | +++ | − |
| 516 | +++ | − |
| 511 | + | − |
| 509 | +++ | − |
| 533 | + | − |
| 532 | ++ | − |
| 530 | +++ | − |

TABLE II

| Example | In Vivo Inhibition of Isolation-induced Aggression |
|---|---|
| Haloperidol | +++ |
| 1 | ++ |
| 230 | +++ |
| 411 | + |
| 503 | +++ |
| 504 | +++ |

TABLE III

| Example | In Vivo Inhibition of PCP-induced Turning | Catalepsy |
|---|---|---|
| Haloperidol | +++ | +++ |
| 504 | +++ | − |

DOSAGE FORMS

Daily dosage ranges from 1 mg to 2000 mg. Dosage forms (compositions) suitable for administration ordinarily will contain 0.5-95% by weight of the active ingredient based on the total weight of the composition.

The active ingredient can be administered orally in solid dosage forms, such as capsules, tablets, and powders, or in liquid dosage forms, such as elixirs, syrups, and suspensions; it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, A. Osol, a standard reference text in this field.

What is claimed is:

1. A method of treating physiological or drug induced psychosis or dyskinesia in a mammal comprising administering to the mammal an antipsychotic or antidyskinetic effective amount of a compound of having the formula:

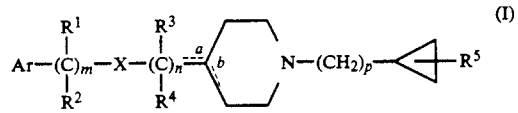

or a pharmaceutically acceptable salt thereof, wherein:
m is 0 to 3;
n is 0 to 3;
provided m and n are not both 0;
p is 0 to 3;
X is O, S, SO, $SO_2$, $NR^6$ or CO;
$R^1 R^3$, and $R^7$ independently are H, alkyl of 1 to 5 carbon atoms, halogen, $NR^{10}R^{11}$, OH, $CO_2H$, carboalkoxy of 2 to 6 carbon atoms, CN, $Ar^1$, alkoxy of 1 to 5 carbon atoms or alkylthio of 1 to 5 carbon atoms;
$R^2$, $R^4$ and $R^8$ independently are H, alkyl of 1 to 5 carbon atoms, carboalkoxy of 2 to 6 carbon atoms, CN, alkoxy of 1 to 5 carbon atoms or $Ar^1$;
provided that $R^1$, $R^2$, $R^3$ and $R^4$ are not alkoxy of 1 to 5 carbon atoms, alkylthio of 1 to 5 carbon atoms, $NR^{10}R^{11}$ or OH when X is O, S, SO, $SO_2$ or $NR^6$;
$R^5$ is H, alkyl, halogen, OH or alkenyl;
$R^6$ is H, alkyl of 1 to 5 carbon atoms or $Ar^1$;
Ar and $Ar^1$ independently are naphthyl, pyridyl, pyrimidyl, indolyl, quinolinyl, isoquinolinyl, or phenyl optionally substituted with alkyl of 1 to 3 carbon atoms, alkoxy of 1 to 3 carbon atoms, haloalkyl of 1 to 3 carbon atoms and 1 to 7 halogen atoms, SH, $S(O)_t$ alkyl of 1 to 3 carbon atoms, where t is 1, 2 or 3, dialkylamino of 2 to 6 carbon atoms, halogen, OH, alkylamino of 1 to 3 carbon atoms, NH₂, CN, NO₂, SO₃H, tetrazole, CO₂H, carboalkoxy of 2 to 6 carbon atoms, CONH₂, SO₂NH₂, COR⁹, CONR¹²R¹³, SO₂NR¹²R¹³, Ar², OAr² or SAr²;

Ar² is naphthyl or phenyl optionally substituted with alkyl of 1 to 3 carbon atoms, haloalkyl of 1 to 3 carbon atoms and 1 to 7 halogen atoms, alkoxy of 1 to 3 carbon atoms, halogen or alkylthio of 1 to 3 carbon atoms;

R⁹, R¹⁰, R¹¹, R¹² and R¹³ independently are H, alkyl of 1 to 5 carbon atoms or phenyl or R¹⁰ and R¹¹ taken together are an alkylene chain of 3 to 6 carbon atoms or R¹² and R¹³ taken together are an alkylene chain of 3 to 6 carbon atoms; and a or b is a double bond or a single bond, provided that both are not double bonds.

2. A method of claim 1 wherein X is CO or O.

3. A method of claim 1 wherein m is O.

4. A method of claim 1 wherein n and p are each 1.

5. A method of claim 1 wherein R³–R⁵ are H.

6. A method of claim 1 wherein Ar is phenyl optionally substituted with halogen, OCH₃, NH₂, NO₂ or another phenyl group.

7. A method of claim 1 wherein:
X is CO or O;
m is 0;
n and p are each 1;
R³–R⁵ are H; and
Ar is phenyl optionally substituted with halogen, OCH₃, NH₂, NO₂ or another phenyl group.

8. A method of claim 7 wherein X is CO.

9. A method of claim 7 wherein Ar is 4-fluorophenyl.

10. A method of claim 7 wherein:
X is CO;
n and p are each 1;
R³, R₄ and R⁵ are H; and
Ar is 4-fluorophenyl.

11. A method of claim 7 wherein X is O.

12. A method of claim 7 wherein:
X is O;
m is 0;
n and p are each 1;
R³, R⁴ and R⁵ are H; and
Ar is 4-fluorophenyl.

13. A method of claim 1 wherein the compound is 1-(cyclopropyl methyl)-4-(2'-(4''-fluorophenyl)-2'-oxoethyl) piperidine.

14. A method of claim 1 wherein the compound is 1-(cyclopropylmethyl)-4-(2'-(4''-fluorophenyl)-2'-oxoethyl) piperidine, hydrobromide salt.

15. A method of claim 1 wherein the compound is 1-(cyclopropylmethyl)-4-(2'-(4''-chlorophenyl)-2'-oxoethyl) piperidine.

16. A method of claim 1 wherein the compound is 1-(cyclopropylmethyl)-4-(2'-(4''-chlorophenyl)-2'-oxoethyl) piperidine, hydrobromide salt.

17. A method of claim 1 wherein the compound is 1-(cyclopropylmethyl)-4-(2'-(4'-fluorophenoxyphenyl) piperidine.

18. A method of claim 1 wherein the compound is 1-(cyclopropylmethyl)-4-(2'-(4'-fluorophenoxyphenyl) piperidine, hydrochloride salt.

19. A method of claim 1 wherein the compound is 1-(cyclopropylmethyl)-4-(2'-(4'-chlorophenoxymethyl)piperidine.

20. A method of claim 1 wherein the compound is 1-(cyclopropylmethyl)-4-(2'-(4'-chlorophenoxymethyl)piperidine, hydrochloride salt.

21. A method of claim 1 wherein the compound is 1-(cyclopropylmethyl)-4-(2'-(4'-nitrophenoxymethyl) piperidine.

22. A method of claim 1 wherein the compound is 1-(cyclopropylmethyl)-4-(2'-(4''-biphenyl)-2'-oxoethyl)-piperidine.

23. A method of claim 1 wherein the compound is 1-(cyclopropylmethyl)-4-(2'-(4''-biphenyl)-2'-oxoethyl)-)piperidine, hydrobromide salt.

24. A method of claim 1 wherein X is O, S, SO, SO₂, NR⁶, or CO.

25. A method of treating physiological or drug induced psychosis or dyskinesia in a mammal by inhibition of the sigma receptor comprising administering to the mammal an antipsychotic or antidyskinetic effective amount of a compound of having the formula:

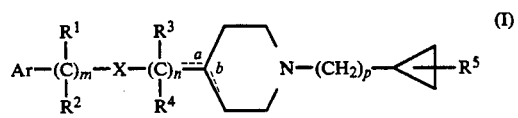

(I)

or a pharmaceutically acceptable salt thereof, wherein:
m is 0 to 3;
n is 0 to 3;
provided m and n are not both O;
p is 0 to 3;
X is O, S, SO, SO₂, NR⁶, CR⁷R⁸, CO, or CHOH;
R¹R³, and R⁷ independently are H, alkyl of 1 to 5 carbon atoms, halogen, NR¹⁰R¹¹, OH, CO₂H, carboalkoxy of 2 to 6 carbon atoms, CN, Ar¹, alkoxy of 1 to 5 carbon atoms or alkylthio of 1 to 5 carbon atoms;
R², R⁴ and R⁸ independently are H, alkyl of 1 to 5 carbon atoms, carboalkoxy of 2 to 6 carbon atoms, CN, alkoxy of 1 to 5 carbon atoms or Ar¹;
provided that R¹, R², R³ and R⁴ are not alkoxy of 1 to 5 carbon atoms, alkylthio of 1 to 5 carbon atoms, NR¹⁰R¹¹ or OH when X is O, S, SO, SO₂ or NR⁶;
R⁵ is H, alkyl, halogen, OH or alkenyl;
R⁶ is H, alkyl of 1 to 5 carbon atoms or Ar¹;
Ar and Ar¹ independently are naphthyl, pyridyl, pyrimidyl, indolyl, quinolinyl, isoquinolinyl, or phenyl optionally substituted with alkyl of 1 to 3 carbon atoms, alkoxy of 1 to 3 carbon atoms, haloalkyl of 1 to 3 carbon atoms and 1 to 7 halogen atoms, SH, S(O)ₜ alkyl of 1 to 3 carbon atoms, where t is 1, 2 or 3, dialkylamino of 2 to 6 carbon atoms, halogen, OH, alkylamino of 1 to 3 carbon atoms, NH₂, CN, NO₂, SO₃H, tetrazole, CO₂H, carboalkoxy of 2 to 6 carbon atoms, CONH₂, SO₂NH₂, COR⁹, CONR¹²R¹³, SO₂NR¹²R¹³, Ar², OAr² or SAr²;

Ar² is naphthyl or phenyl optionally substituted with alkyl of 1 to 3 carbon atoms, haloalkyl of 1 to 3 carbon atoms and 1 to 7 halogen atoms, alkoxy of 1 to 3 carbon atoms, halogen or alkylthio of 1 to 3 carbon atoms;

R⁹, R¹⁰, R¹¹, R¹² and R¹³ independently are H, alkyl of 1 to 5 carbon atoms or phenyl or R¹⁰ and R¹¹ taken together are an alkylene chain of 3 to 6 carbon atoms or R¹² and R¹³ taken together are an alkylene chain of 3 to 6 carbon atoms; and a or b is a double bond or a single bond, provided that both are not double bonds.

* * * * *